US012584898B2

(12) United States Patent
Molyneux et al.

(10) Patent No.: US 12,584,898 B2
(45) Date of Patent: Mar. 24, 2026

(54) SYSTEM AND METHOD FOR CHARACTERIZING, DETECTING, AND MONITORING PATHOGEN POPULATIONS IN AN INDOOR ENVIRONMENT

(71) Applicant: Poppy Health, Inc., Mountain View, CA (US)

(72) Inventors: Sam D. Molyneux, Mountain View, CA (US); Elizabeth Caley, Mountain View, CA (US); Daniela Bezdan, Mountain View, CA (US); Ricardo Vidal, Mountain View, CA (US); Nathan Volman, Mountain View, CA (US); Tae Joon Yi, Mountain View, CA (US)

(73) Assignee: Poppy Health, Inc., Mountain View, CA (US)

( * ) Notice: Subject to any disclaimer, the term of this patent is extended or adjusted under 35 U.S.C. 154(b) by 1004 days.

(21) Appl. No.: 17/728,472

(22) Filed: Apr. 25, 2022

(65) Prior Publication Data

US 2022/0341909 A1      Oct. 27, 2022

Related U.S. Application Data

(60) Provisional application No. 63/178,712, filed on Apr. 23, 2021.

(51) Int. Cl.
G08B 23/00      (2006.01)
C12Q 1/6888      (2018.01)
(Continued)

(52) U.S. Cl.
CPC ....... G01N 33/0075 (2013.01); C12Q 1/6888 (2013.01); G01N 33/0036 (2013.01); G01N 33/497 (2013.01)

(58) Field of Classification Search
CPC ......... H01M 10/0569; H01M 10/0525; H01M 2300/0028; H01M 2300/0025; H01M 10/0567; H01M 10/052; Y02E 60/10
See application file for complete search history.

(56) References Cited

U.S. PATENT DOCUMENTS 7,302,313 B2 * 11/2007 Sharp ................. G01N 33/0075
                                          700/282
7,578,973 B2      8/2009 Call et al.
(Continued)

FOREIGN PATENT DOCUMENTS

CN      111662816 A      9/2020
CN      112014528 A      12/2020
(Continued)

OTHER PUBLICATIONS

International Search Report and Written Opinion for International Patent Application No. PCT/US2021/64875 mailed on Mar. 29, 2022; 13 pages.
(Continued)

*Primary Examiner* — Toan N Pham
(74) *Attorney, Agent, or Firm* — Run8 Patent Group, LLC; Peter Miller; Leah Raddatz

(57) ABSTRACT

One variation of a method for detecting pathogens includes: accessing a timeseries of pathogen data for a pathogen, in a set of pathogens, derived from a series of pathogen samples collected in an environment during a time period; characterizing a pathogen profile, representative of changes in pathogen level of the first pathogen in the environment during the time period, based on the timeseries of pathogen data; accessing a baseline pathogen profile representative of changes in pathogen levels of the set of pathogens in the environment during an initial time period preceding the time period; characterizing a difference between the pathogen profile and the baseline pathogen profile; and, in response to
(Continued)

the difference exceeding a threshold difference, selecting a mitigation action configured to reduce pathogen levels of the first pathogen and transmitting a prompt to execute the mitigation action to a user associated with the indoor environment.

20 Claims, 5 Drawing Sheets

(51) Int. Cl.
    *G01N 33/00*         (2006.01)
    *G01N 33/497*      (2006.01)

(56)           References Cited

U.S. PATENT DOCUMENTS

| | | | |
|---|---|---|---|
| 7,633,606 | B2 | 12/2009 | Northrup et al. |
| 8,272,280 | B2 | 9/2012 | Jones, Jr. |
| 8,539,840 | B2 | 9/2013 | Ariessohn et al. |
| 8,578,796 | B2 | 11/2013 | Cho |
| 8,689,648 | B1 | 4/2014 | Heff |
| 9,005,989 | B2 * | 4/2015 | Harper .................... G01N 21/64 |
| | | | 436/805 |
| 9,689,792 | B1 | 6/2017 | Sickenberger et al. |
| 9,880,159 | B2 * | 1/2018 | Powers ............. B01L 3/502715 |
| 10,919,047 | B2 | 2/2021 | Mainelis et al. |
| 11,300,484 | B1 | 4/2022 | Bango |
| 2011/0252897 | A1 | 10/2011 | Swenson et al. |
| 2012/0174650 | A1 | 7/2012 | Ariessohn et al. |
| 2021/0208062 | A1 | 7/2021 | Linden |
| 2021/0324485 | A1 | 10/2021 | Hodges et al. |
| 2022/0034763 | A1 | 2/2022 | Dutta |
| 2022/0091010 | A1 | 3/2022 | Wystup et al. |
| 2023/0176024 | A1 * | 6/2023 | Molyneux ........ G01N 35/00722 |
| | | | 222/52 |

FOREIGN PATENT DOCUMENTS

| | | | |
|---|---|---|---|
| JP | 2017096727 | A | 6/2017 |
| KR | 20110097199 | A | 8/2011 |
| WO | 2019018559 | A1 | 1/2019 |
| WO | 2022047340 | A1 | 3/2022 |
| WO | 2022081543 | A1 | 4/2022 |

OTHER PUBLICATIONS

M. Z. Bazant, J. W. Bush, A guideline to limit indoor airborne transmission of covid-19. Proceedings of the National Academy of Sciences. 118 (2021), doi:10.1073/pnas.2018995118.

Non-Final Office Action for U.S. Appl. No. 17/559,257 mailed on Jun. 8, 2022; 7 pages.

* cited by examiner

SYSTEM AND METHOD FOR CHARACTERIZING, DETECTING, AND MONITORING PATHOGEN POPULATIONS IN AN INDOOR ENVIRONMENT

CROSS-REFERENCE TO RELATED APPLICATIONS

This application claims the benefit of U.S. Provisional Application No. 63/178,712, filed on 23 Apr. 2021, which is incorporated in its entirety by this reference.

TECHNICAL FIELD

This invention relates generally to the field of metagenomics and more specifically to a new and useful method for pathogen detection in the field of metagenomics.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
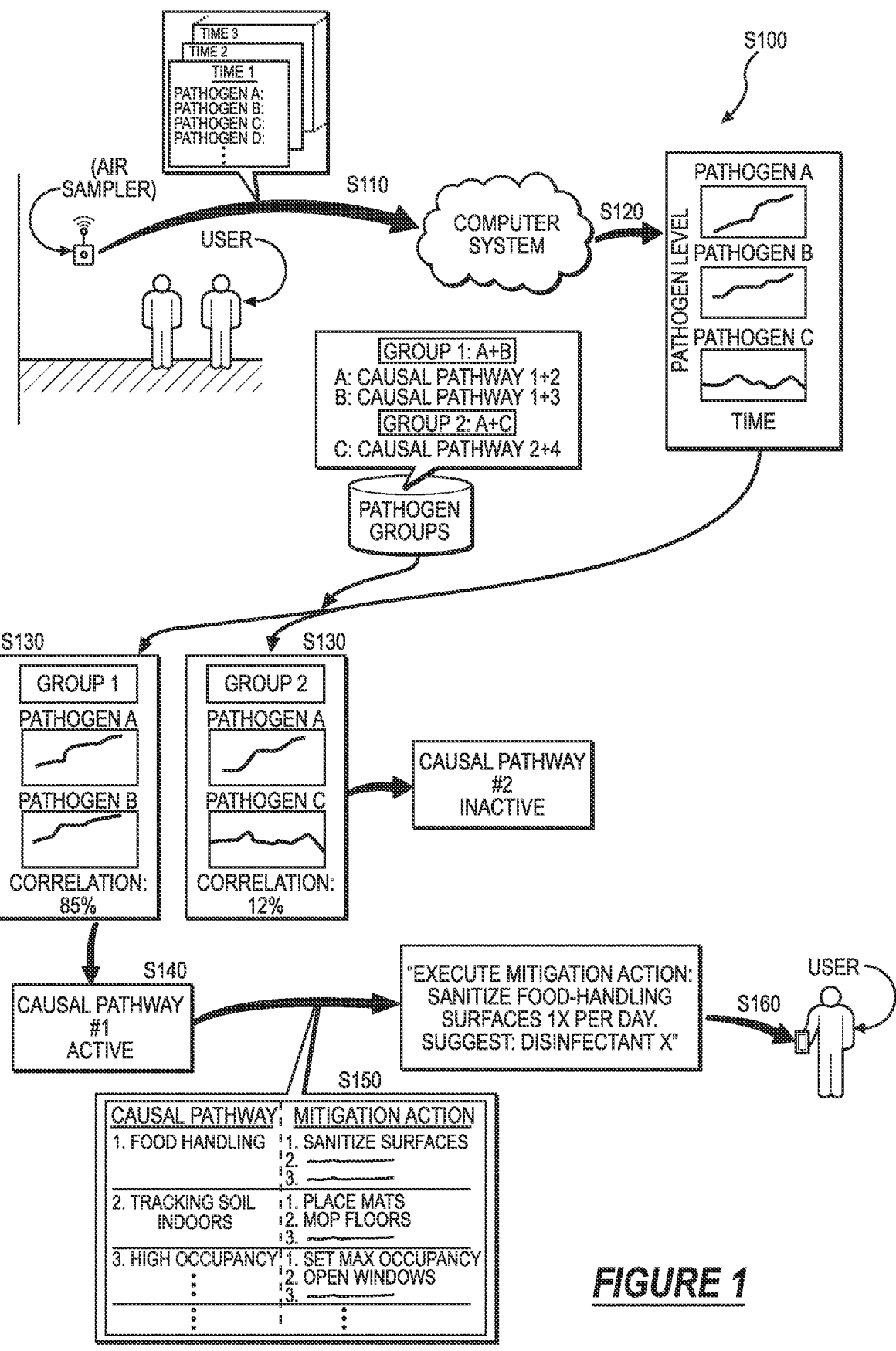
FIG. 1 is a flowchart representation of a method.
Figure 2A:
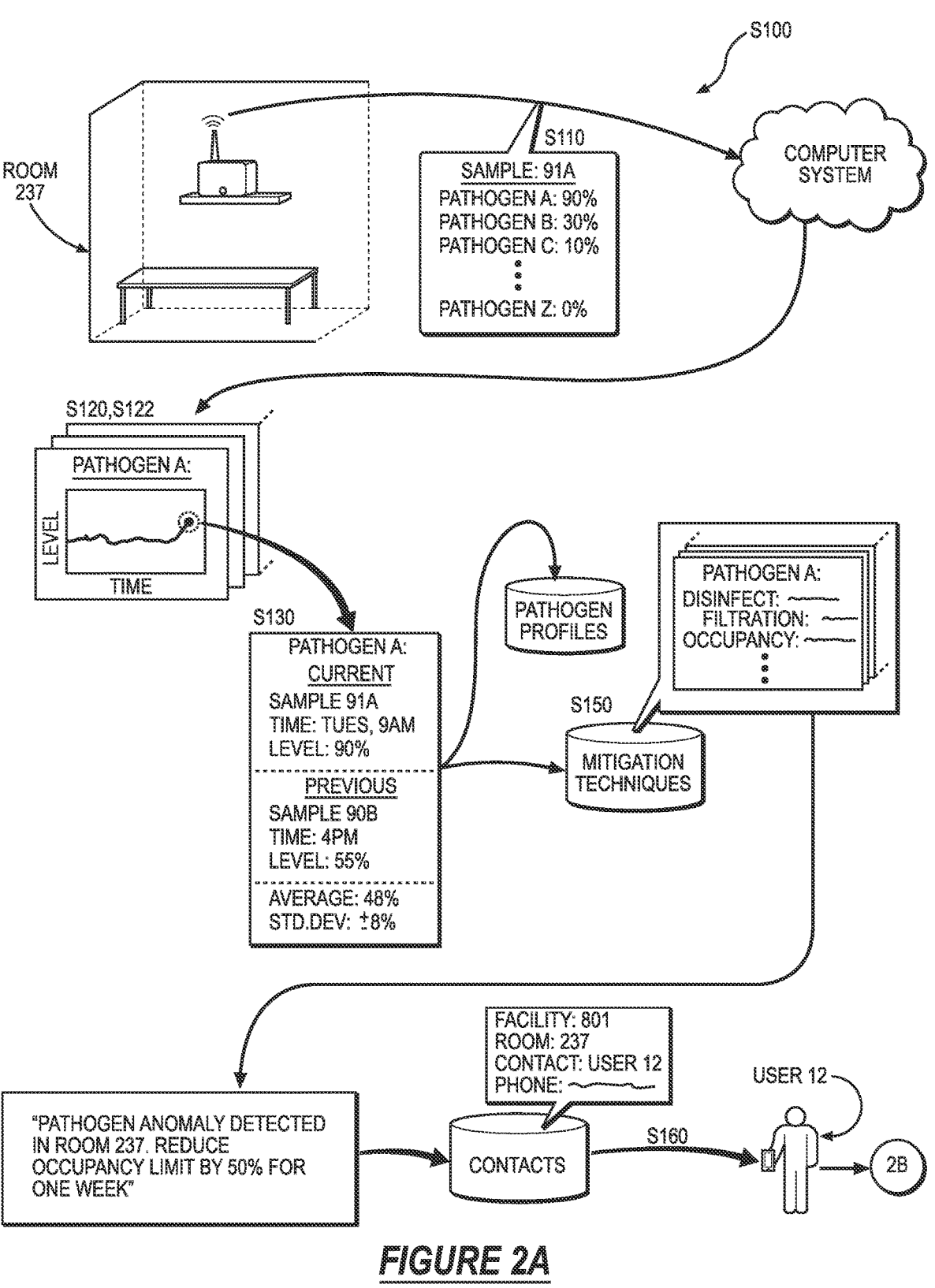
FIGS. 2A and 2B are flowchart representations of the method.
Figure 2B:
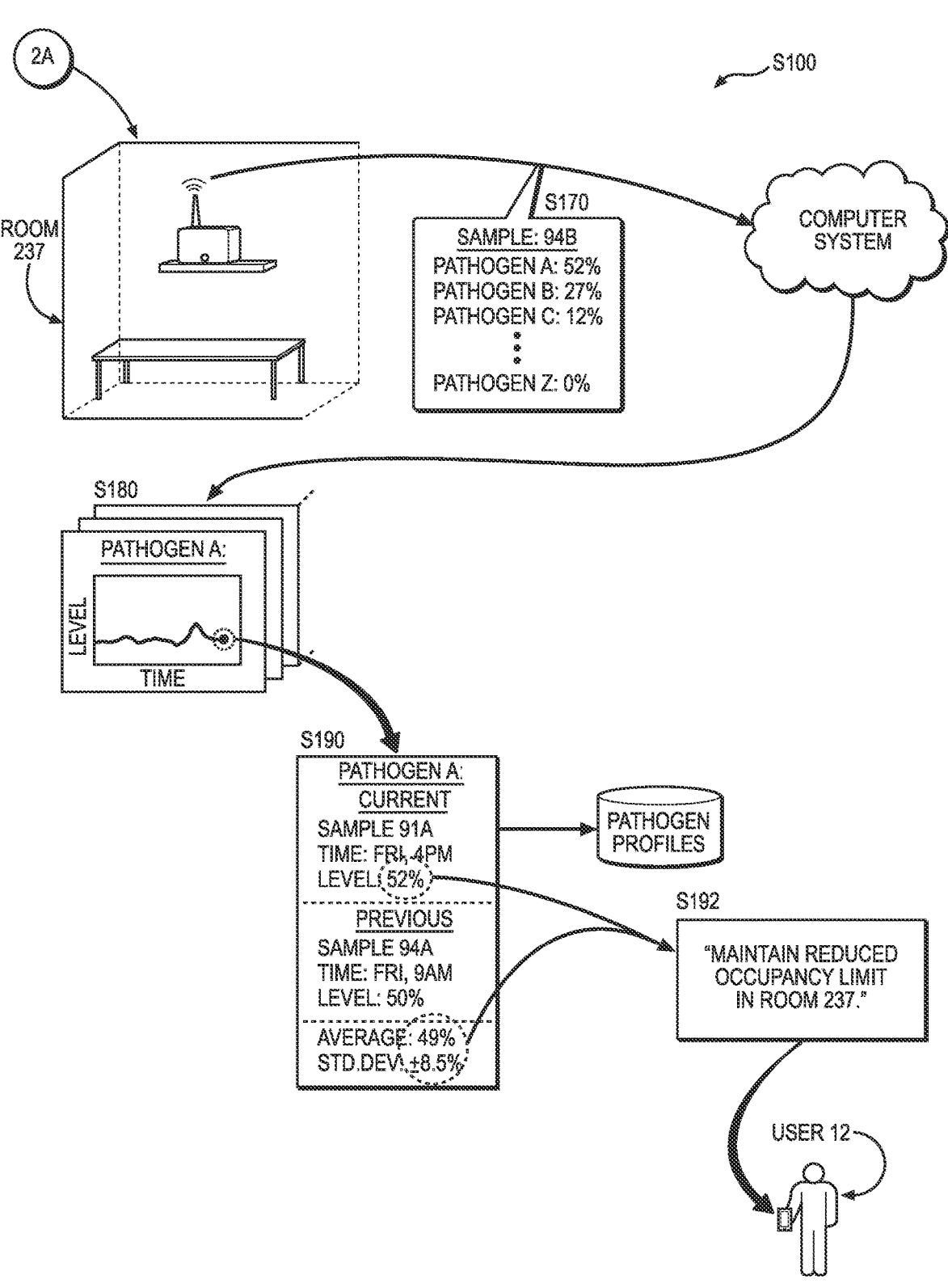
Figure 3:
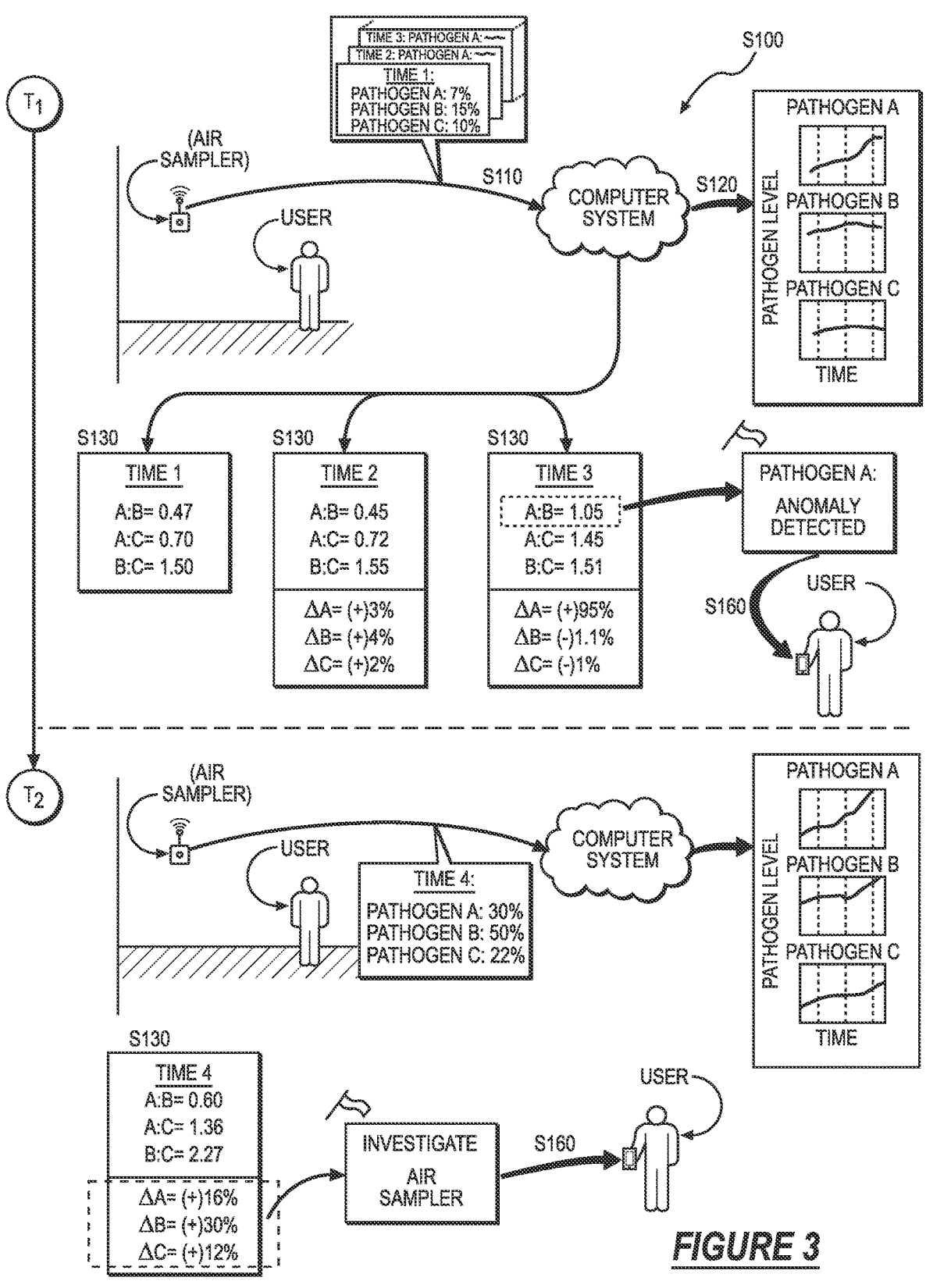
FIG. 3 is a flowchart representation of the method.
Figure 4:
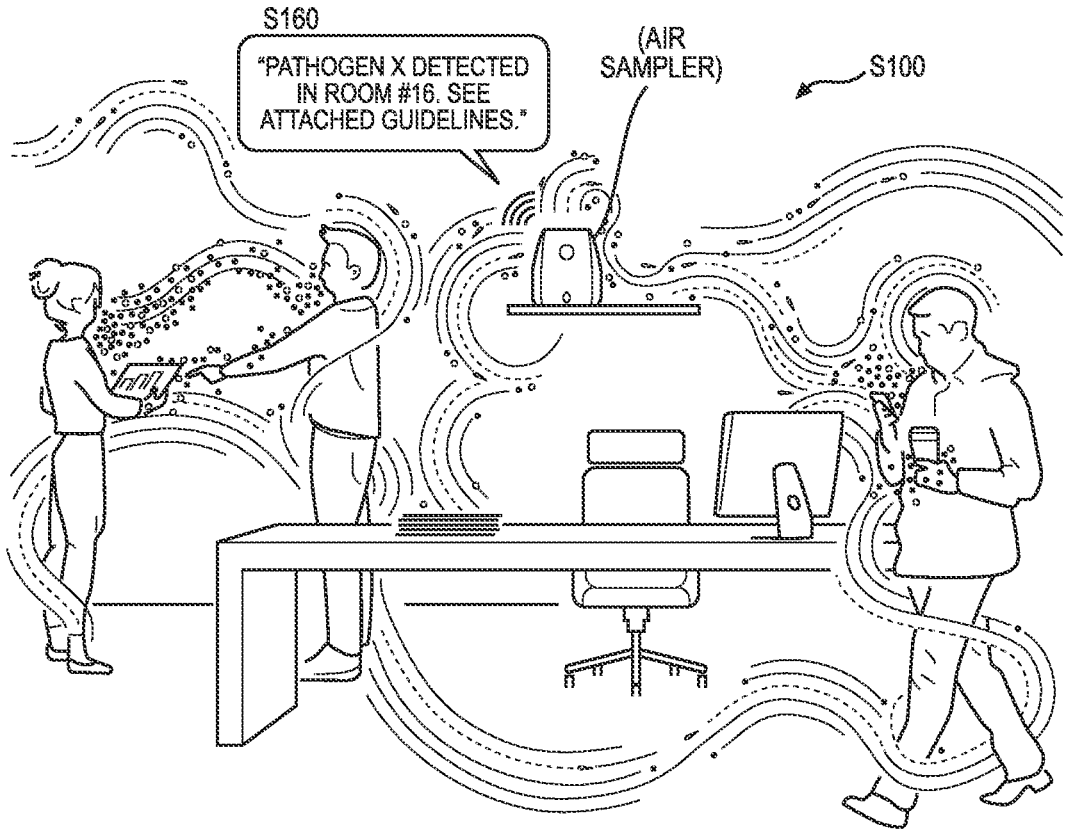
FIG. 4 is a flowchart representation of the method.

As shown in FIGS. 1, 2A, 2B, 3, and 4, a method S100 includes: accessing a timeseries of pathogen data derived from a series of pathogen samples collected by an air sampler, installed in an indoor environment, during a first time period, and representing levels of a set of microbes (e.g., pathogens and/or nonpathogenic microbes) in Block S110; and, for each microbe, in the set of microbes, deriving a population curve, in a set of population curves, representing changes in a population of the microbe present in the indoor environment during the first time period based on the timeseries of pathogen data in Block S120. The method S100 further includes, for a first subset of microbes in the set of microbes: characterizing a first correlation between a first subset of population curves, in the set of population curves, corresponding to the first subset of microbes in Block S130; based on the first correlation, predicting a first causal pathway for an increase in populations of the first subset of microbes during the first time period based on characteristics common within the first subset of microbes in Block S140; identifying a first mitigation action, in a set of mitigation actions, linked to suppression of the first causal pathway in Block S150; generating a prompt to execute the first mitigation action in the indoor environment; and transmitting the prompt to a user associated with the indoor environment in Block S160.

One variation of the method S100 includes: accessing a first timeseries of pathogen data for a first pathogen, in a set of pathogens, and derived from a series of pathogen samples collected during a first time period by an air sampler installed in an indoor environment in Block S110; characterizing a first pathogen profile, in a first set of pathogen profiles, of the indoor environment during the first time period based on the first timeseries of pathogen data, the first pathogen profile representative of changes in pathogen level of the first pathogen in the indoor environment during the first time period in Block S120; accessing a baseline pathogen profile of the indoor environment, the baseline pathogen profile representative of changes in pathogen levels of the set of pathogens during an initial time period preceding the first time period in Block S122; and characterizing a first difference between the first pathogen profile and the baseline pathogen profile in Block S130. In this variation, the method S100 further includes, in response to the first difference exceeding a threshold difference: selecting a first mitigation action, in a set of mitigation actions, configured to reduce pathogen levels of the first pathogen, based on the first difference in Block S150; generating a prompt to execute the first mitigation action in the indoor environment; and transmitting the prompt to a user associated with the indoor environment in Block S160.

One variation of the method S100 includes: accessing a first timeseries of pathogen data for a first pathogen, in a set of pathogens, and derived from a series of pathogen samples collected from a defined space at a first frequency during a first time period in Block S110; characterizing a first pathogen profile for the defined space during the first time period based on the first timeseries of pathogen data in Block S120; accessing a baseline pathogen profile of the defined space, the baseline pathogen profile representative of changes in pathogen levels of the set of pathogens during an initial time period preceding the first time period in Block S122; and characterizing a first difference between the first pathogen profile and the baseline pathogen profile in Block S130. The method S100 further includes, in response to the first difference exceeding a threshold difference: selecting a first mitigation action, in a set of mitigation actions, based on the first difference in Block S150; generating a prompt to implement the first mitigation action in the defined space; and transmitting the prompt to a user associated with the defined space in Block S160.

In one variation, the method S100 further includes: accessing a second timeseries of pathogen data for the first pathogen and derived from a second series of pathogen samples collected from the defined space during a second time period succeeding the first time period in Block S170; characterizing a second pathogen profile for the defined space during the second time period based on the second timeseries of pathogen data in Block S180; and characterizing a second difference between the second pathogen profile and the baseline pathogen profile in Block S190. The method S100 further includes, in response to the second difference falling below the threshold difference, confirming implementation of the first mitigation action for the first pathogen in the defined space in Block S192.

In one variation, the method S100 includes: accessing a first pathogen level of a first pathogen, in a set of pathogens, detected in a first pathogen sample collected during a first time period in Block S110; accessing a second pathogen level of the first pathogen, detected in a second pathogen sample collected during a second time period succeeding the first time period, the second pathogen level exceeding the first pathogen level in Block S110; and characterizing a difference between the first pathogen level and the second pathogen level in Block S130. In this variation, the method S100 further includes, in response to the difference exceeding a threshold difference: generating a prompt to implement a mitigation action based on the difference; and transmitting the prompt to a user associated with the defined space in Block S160.

2. Applications

Generally, Blocks of the method S100 can be executed by a remote computer system in conjunction with an air sampler (hereinafter "the system") to: identify pathogens present in a pathogen sample collected from an enclosed environment (e.g., an enclosed space within a commercial, retail, office, or industrial building) occupied by the air sampler; interpret changes in presence and/or magnitude of pathogens present in the enclosed environment based on signals in the pathogen sample; and selectively generate and distribute prompts related to detection and/or mitigation of these pathogens detected in the enclosed environment.

In particular, once deployed (e.g., permanently or temporarily installed) in a particular space, the air sampler can ingest air from the space over time and draw this air over an internal collection subsystem to collect pathogen samples from the space, such as once per day, once per hour, once per minute, or continuously. An internal genetic material load detector, selective pathogen detector, or DNA sequencer within the air sampler can then process these pathogen samples to detect presence and/or magnitude (e.g., pathogen level) of various genetic material (or viral and/or bacterial pathogens specifically) in the space, and the air sampler can then assemble detected presence and/or magnitudes of genetic material thus detected in the space over time into timeseries pathogen data representing presence and/or magnitude of genetic material in air within the space over time.

Alternatively, pathogen samples collected by the air sampler can be intermittently returned to a lab for processing and generation of timeseries pathogen data.

The system (e.g., the remote computer system) can then: access this timeseries of pathogen data—thus representing presence and/or magnitude of a set of pathogens detectable in the space; and characterize a pathogen profile—representative of magnitudes and/or changes in pathogen levels in a set of pathogens detectable in the space—during the sample interval represented in this timeseries of pathogen data. Based on this pathogen profile, the system can characterize changes in pathogen levels for pathogens in the space as a function of time. The system can also fuse this pathogen profile with other data collected from the space, such as timeseries human occupancy and ambient condition data to characterize changes in particular pathogens as a function of air temperature, ambient humidity, or human occupancy within the space.

Furthermore, the system can execute this process during initial deployment of the air sampler to the space (or during another setup or calibration period) in order to capture baseline pathogen timeseries data for the space and to derive a baseline pathogen profile for the space from these baseline pathogen timeseries data. The system can subsequently execute the method to capture additional pathogen timeseries data and to derive additional pathogen profiles for the space over time. The system can then compare current pathogen levels (represented in a current pathogen profile) to baseline pathogen levels (represented in the baseline pathogen profile) to: detect anomalies in pathogen levels of pathogens; estimate when changes in pathogen levels occur in the space; and identify triggers (e.g., causes) of these changes. Over time, the system can continuously update the baseline and/or current pathogen profile based on new pathogen data collected from pathogen samples.

By leveraging this timeseries of pathogen data, the system can extract deeper insights into pathogen spread and/or containment within this particular space. For example, rather than reporting a raw pathogen level of a pathogen in the space at a particular timepoint, the system can report a change in pathogen level of this pathogen since a prior timepoint, which may be more indicative of health changes in the space and more actionable for users associated with the space.

The system can continue monitoring pathogen levels of the space over time to (regularly, continuously) characterize the pathogen profile for this space and implement this pathogen profile to identify mitigation need and to serve mitigation actions to users associated with the space in near real-time, thus enabling these users to monitor and mitigate instances of pathogen anomalies, such as due to an elevated pathogen level for a particular pathogen in the space. The system can then update the pathogen profile for this space over time as the system receives or captures additional information (e.g., pathogen data, environmental data, user feedback) regarding this space.

Further, the system can derive correlations between pathogen data (e.g., pathogen levels recorded over time) and environmental controls in a particular space to: identify mitigation actions (e.g., based on these environmental controls) best matched to the space; and predict changes in pathogen levels in the space based on these environmental controls. In particular, the system can leverage the timeseries of pathogen data and recorded environmental controls manipulated during collection of the timeseries of pathogen data to derive a space-specific pathogen model linking environmental controls with pathogen levels in this space. For example, the system can: access the timeseries of pathogen data—including pathogen levels of a particular pathogen—recorded over a particular time period; access a series of environmental data corresponding to a set of environmental controls (e.g., occupancy, air filtration, air and/or surface disinfection, air dilution); and transform the series of environmental data into timestamped changes in (one or more) environmental controls; synchronize the timeseries of pathogen data and timestamped changes in environmental controls; and implement regression, machine learning, deep learning, and/or other techniques to derive correlations between environmental controls and pathogen levels in this particular space. The system can then compile these correlations into a space-specific pathogen model configured to link patterns or changes to these environmental controls to changes and/or patterns of pathogen levels in this space.

The system can therefore link changes in pathogen levels in a space—which may be indicative of health changes in this space—to physical, environmental changes (i.e., changes in environmental controls) in the space, and thereby leverage this information to make suggestions regarding environmental controls in the space. Thus, by leveraging pathogen data in combination with environmental data for the space, the system can extract deeper insights into the spread and/or containment of pathogens in this space.

The method S100 is described below as executed by a remote computer system in conjunction with the air sampler to monitor and detect pathogens present in an air sample collected from a space (e.g., an enclosed space). However, the remote computer system can implement similar methods and techniques to monitor and detect pathogens present in other types of samples collected from the space, such as in a surface sample or a water sample collected from the space.

Further, the method S100 is described below as executed by a remote computer system in conjunction with the air sampler to monitor and detect pathogens present in an indoor environment. However, the remote computer system can implement similar methods and techniques to monitor and detect any type of microorganism (or "microbe")— including pathogenic and/or non-pathogenic microbes— present in the indoor environment, such as bacteria, viruses, fungi, and/or any other type of microbe.

3. Air Sampler

The system can include an air sampler configured to draw air from a surrounding space and through an inlet of the air sampler to collect a pathogen sample.

In one implementation—as described in U.S. patent application Ser. No. 17/709,213, filed on 30 Mar. 2022, which is incorporated in its entirety by this reference—the air sampler can be configured to include an air-capture module configured to draw air from the environment through the inlet of the body via electrostatic forces. This "electrostatic air sampler" can include: a charging element; a sampling medium in the form of a collector plate; and a power supply air-capture module configured to apply a voltage across the collector plate. For example, the electrostatic air sampler can include: an inlet configured to transfer a bioaerosol sample from a surrounding space into the electrostatic air sampler; a collector plate configured to receive the bioaerosol sample and collect pathogens present in the bioaerosol sample; and a corona wire configured to cooperate with the collector plate to draw the bioaerosol sample through the inlet via electrostatic forces. In particular, in this example, the air sampler can be configured to supply a voltage between the corona wire and the collector plate to enable ionization of particles present in the bioaerosol sample, thereby accelerating these particles through the inlet and onto the collector plate.

In one example of the preceding implementation, the air sampler can include: a sampler housing defining an inlet and an outlet; a tunnel extending between the inlet and the outlet within the sampler housing; a charge electrode arranged within the tunnel proximal the inlet; a sampler cartridge receptacle arranged proximal the fluid outlet within the sampler housing and including a cartridge terminal; and a power supply configured to drive a voltage between the charge electrode and the cartridge terminal. In this example, the pathogen detection system can further include a sampler cartridge including: a substrate (e.g., a printed circuit board); a collector plate arranged on the substrate and configured to collect charged bioaerosols moving through the tunnel; and a connector configured to transiently engage the sampler cartridge receptacle to locate the substrate and the collector plate within the tunnel and electrically couple the collector plate to the cartridge terminal.

Alternatively, in another implementation, the air sampler can be configured to include an air-capture module including a pump coupled to the inlet of the air sampler and configured to draw air from the inlet and onto a sampling medium within a body of the air sampler at a target rate (e.g., once cubic foot per second). This "pump-based air sampler" can include a sampling medium in the form of a filter cartridge (e.g., a PTFE filter cassette). For example, the pump-based air sampler can actuate the pump to draw air through the inlet and through the filter cartridge such that particles in the air collect on a filter within the filter cartridge. The pump-based air sampler can continue to actuate the pump to dry and thus concentrate these particles on the filter over a sampling time period, such as of a predefined duration (e.g., 30 seconds).

In each of these implementations, the air sampler can further include: a controller including a set of electronics and configured to selectively actuate components of the air sampler; and a communication module configured to transmit data between the air sampler, a set of external devices (e.g., other air samplers and/or devices installed in the environment, a mobile device, a local computing device), and/or a computer system (e.g., a local server, a remote computer system).

3.1 Deployment

In one implementation, the air sampler can be installed within a particular space within a facility—such as fixed to a wall, mounted on a stand, or standing on a floor of a particular room. Alternatively, the air sampler can be coupled with a mobile apparatus (e.g., a manual or autonomously cart, an autonomous aerial vehicle) configured to transport the air sampler about a space or facility. For example, the air sampler can be mounted (e.g., transiently, permanently) to a mobile robot (e.g., a UGV) configured to autonomously navigate between different rooms within an office building to monitor pathogen levels across each of these rooms.

Alternatively, the system can include a set of air samplers installed throughout a particular facility (e.g., one per floor in an office building). For example, the system can include a docking station (e.g., a charging docking station) configured to house a set of air samplers, such that each air sampler can be deployed from the docking station to a particular space (e.g., an office, a classroom, a store, a bathroom) within a larger facility (e.g., an office building, a school, a mall, an airport).

3.2 Pathogen Detection

The system can be configured to detect presence and/or pathogen levels (e.g., magnitude) of a set of pathogens within the space.

In one implementation, the air sampler can be configured to process these pathogen samples for diagnostics and/or genetic sequencing directly within the air sampler. In particular, in this implementation, the air sampler can include: a detection module configured to receive the pathogen sample for genetic testing; and a handoff configured to transfer a collected pathogen sample from the sampling medium to the detection module for pathogen detection (e.g., via genetic testing). Further, the detection module can include a processing stage configured to process the pathogen sample in preparation for diagnostics and/or genetic sequencing. For example, at an expiration of a sampling window, the air sampler can transfer a pathogen sample from the sampling medium to the processing stage of the detection module via the handoff. Then, at the processing stage, the air sampler can: lyse DNA and/or RNA fragments in the pathogen sample; concentrate these DNA and/or RNA fragments within the pathogen sample; and compile these fragments from the pathogen sample into a genetic library (e.g., a DNA and/or RNA library) for genetic sequencing. The pathogen sample—prepared into the genetic library—can then be passed through a genetic sequencer (e.g., a nanopore genetic sequencer, a LAMP reactor) configured to identify a set of pathogens present in the pathogen sample.

Alternatively, in another implementation, the air sampler can be configured to store this pathogen sample for further processing at a remote location. In this variation, the air sampler can be configured to collect the pathogen sample at the sampling medium and store the pathogen sample (e.g., in a storage module) within the air sampler for later collection. For example, the air sampler can be configured to: collect a pathogen sample each day for a week (e.g., to collect 7 pathogen samples, one for each day of the week); and store each pathogen sample on a different cartridge within the air sampler. In particular, in this example, the air sampler can be configured to include a carousel housing a set of cartridges, such that the air sampler can actuate the carousel each day to rotate a fresh (i.e., clean, empty) cartridge into a sampling position, each cartridge linked to a corresponding day of the week. A user (e.g., associated with the space) can then: collect the set of cartridges from the carousel at an end of the week for further testing offsite; and refill the carousel with a new set of cartridges for the next week.

3.3 Sampling Frequency

In one implementation, the system can trigger collection of pathogen samples at the air sampler intermittently, such as at set sampling intervals (e.g., once per hour, once per day, once per week) and over a set sampling window (e.g., 1-hour, 24-hours, 1-week). Alternatively, in another implementation, the system can selectively choose times to collect pathogen samples, such as in response to detecting a pathogen anomaly in a particular space.

For example, the air sampler can be configured to collect pathogen samples at a set frequency of once per day over 8-hour sampling windows. At an end of the day, the system can: trigger analysis of a pathogen sample collected during the day at the air sampler; access a first pathogen level of a first pathogen detected in the pathogen sample; and access a baseline pathogen level of the first pathogen (e.g., stored in the pathogen profile for this space). Then, in response to the first pathogen level exceeding a baseline pathogen level of the first pathogen, the system can: identify a mitigation action matched to this pathogen in this space; suggest implementation of the mitigation action to a user associated with the space; and, the next day, automatically trigger collection of pathogen samples at a set frequency of once per hour over 1-hour sampling windows. Thus, by increasing the frequency of detection, the system can: further monitor the pathogen level of this particular pathogen; and evaluate whether the suggested mitigation action is effective for mitigating this pathogen in this space.

4. Anomaly Detection

The system can be configured to detect anomalies in pathogen levels in a particular space. For example, the air sampler can be installed in a conference room of an office building. The air sampler can be configured to continuously draw air from the conference room onto the sampling medium over a sampling window (e.g., 1 minute, 1 hour, 1 day, 1 week) to collect and concentrate a pathogen sample onto the sampling medium. Upon expiration of this sampling window, the air sampler can terminate collection of this pathogen sample and pass the pathogen sample to a detection module within the air sampler for local analysis (e.g., via genetic sequencing). Alternatively, the system can alert a user (e.g., a manager, an administrator, a worker) to collect this pathogen sample for further analysis offsite.

Upon completion of analysis of this pathogen sample, the system can characterize a first pathogen level (i.e., pathogen load) of the pathogen sample, the first pathogen level corresponding to a first pathogen, in a set of pathogens, detectable by the air sampler. Then, in response to the first pathogen level exceeding a threshold pathogen level, the system can flag this first pathogen level as a pathogen anomaly requiring further action and/or investigation. Therefore, the system can identify pathogen anomalies responsive to detected pathogen levels exceeding this predefined threshold pathogen level.

4.1 Predefined Pathogen Threshold

In order to detect anomalies in pathogen levels in the space, the system can assign a threshold pathogen level to a particular pathogen, in a set of pathogens, detectable in the space. In one implementation, the system can assign a generic threshold pathogen level to a particular pathogen based on known or global pathogen data for this particular pathogen, such as corresponding to a pathogen level that is considered dangerous for this particular pathogen.

Additionally and/or alternatively, in another implementation, the system can leverage basic information about the space—such as size, location, and/or average occupancy in the space—to identify a threshold pathogen level for a particular pathogen in this particular space. For example, the system can: access a first size (e.g., height, length, width, floor area, volume) of a first indoor environment; access a first average occupancy level (e.g., occupant density, number of occupants) of the first indoor environment; and assign a first threshold pathogen level for a first pathogen, in a set of pathogens, in the first indoor environment based on the first size and the first average occupancy level, such as by calculating the first threshold pathogen level based on a global pathogen model, the first size, and the first average occupancy level, and/or by selecting the first threshold pathogen level from a set of predefined threshold pathogen levels assigned to indoor environments of varying sizes and/or occupancy levels. Additionally, in this example, the system can: access a second size of a second indoor environment; access a second average occupancy level of the second indoor environment; and assign a second threshold pathogen level for the first pathogen in the second indoor environment based on the second size and the second average occupancy level. The system can thus identify a threshold pathogen level—for a particular pathogen and/or set of pathogens—matched to characteristics of the indoor environment.

4.2 Environment-Specific: Baseline Pathogen Thresholds

In yet another implementation, the system can set a threshold pathogen level, for a particular pathogen in the space, based on baseline pathogen levels recorded during a setup time period. For example, during an initial setup time period (e.g., one week, one month) for a space, the system can: record a first pathogen level (e.g., baseline pathogen load) for a first pathogen detected in a first pathogen sample collected during a first test sampling time period within the initial setup time period; record a second pathogen level for the first pathogen detected in a second pathogen sample collected during a second test sampling time period succeeding the first test sampling time period within the initial setup time period; record a third pathogen level for the first pathogen detected in a third pathogen sample collected during a third test sampling time period succeeding the second test sampling time period within the initial setup time period; and calculate a first baseline pathogen level for the first pathogen in the space based on the first pathogen level, the second pathogen level, and the third pathogen level. The system can then repeat this process for each pathogen, in a set of pathogens detectable in the space, to generate a baseline pathogen profile for the space including a set of baseline pathogen levels linked to the set of pathogens.

Later, during a live time period succeeding the initial setup time period, the system can: access a first pathogen level of the first pathogen detected in a fourth pathogen sample collected during the live period: access the baseline pathogen profile generated for the space during the initial setup time period; and, in response to the first pathogen level of the first pathogen exceeding the first baseline pathogen level of the first pathogen stored in the baseline pathogen profile, flag this first pathogen level as a pathogen anomaly requiring further investigation and/or action.

In one implementation, the system can leverage baseline pathogen levels recorded during the initial setup period in a space to identify patterns (e.g., changes) in pathogen levels over time. The system can then leverage these patterns to identify baseline pathogen levels for a particular timepoint (e.g., time of day, day of the week) in this space, such as for a particular pathogen, a particular subset of pathogens, or all pathogens detectable in this space. In particular, the system can: identify patterns of volatility in these baseline pathogen levels throughout the initial setup period; and leverage these patterns during the live period to identify particular periods of time during which particular pathogen levels may exhibit volatility (e.g., spikes in pathogen level). For example, the system can record a timeseries of pathogen data during a setup period for a particular space. The system can then implement statistical techniques (e.g., regression), machine learning, deep learning, and/or other techniques to derive correlations between time values (e.g., time of day, day of the week) and pathogen levels in this particular space based on the timeseries of pathogen data. Later, during a live period succeeding the setup period, the system can leverage these correlations to both predict changes in pathogen levels over time and to identify expected changes (e.g., increases, decreases) in pathogen levels as detected in the space. Thus, in this example, the system can: identify a particular baseline pathogen level at a particular time (e.g., time of day, day of the week) based on these correlations; and compare a detected pathogen level, corresponding to a pathogen sample collected at the particular time, to this baseline pathogen level to identify whether the pathogen sample corresponds to a pathogen anomaly.

In another implementation, the system can set a threshold pathogen level, for a particular pathogen detectable in the space, based on a prior detected pathogen level for this particular pathogen. For example, the system can access: a first pathogen level of a first pathogen, in a set of pathogens, collected during a first sampling time period; a second pathogen level of the first pathogen collected during a second sampling time period succeeding the first sampling time period; and a third pathogen level of the first pathogen collected during a third sampling time period succeeding the second sampling time period. The system can then: characterize a first difference between the second pathogen level and the first pathogen level; characterize a second difference between the second pathogen level and the first pathogen level; and, in response to the second difference exceeding a threshold difference, flag the third pathogen level of the first pathogen as a pathogen anomaly. The system can therefore detect pathogen anomalies in the space by comparing current pathogen levels of a set of pathogens and prior pathogen levels of the set of pathogens in this space.

4.3 Baseline Pathogen Profile

In one implementation, the system can leverage a time-series of pathogen data collected during sampling periods to characterize a (current) pathogen profile for a set of pathogens detectable in a space. In particular, the system can: compare current trends in pathogen levels (e.g., for a particular pathogen or set of pathogens) to historical trends in pathogen levels in this space; and detect changes in pathogen levels over time based on this comparison to identify pathogen anomalies (e.g., pathogen level anomalies) in this space and/or to identify triggers associated with these pathogen anomalies.

For example, the system can access a first timeseries of pathogen data collected over an initial time period, the first timeseries of pathogen data including: a first pathogen level of a first pathogen, in a set of pathogens, collected during a first sampling time period; a second pathogen level of the first pathogen collected during a second sampling time period succeeding the first sampling time period; and a third pathogen level of the first pathogen collected during a third sampling time period succeeding the second sampling time period. The system can then: characterize a first pathogen profile—representative of changes in pathogen levels of the first pathogen during the first time period—based on the first timeseries of pathogen data (e.g., the first pathogen level, the second pathogen, and the third pathogen level), such as by interpolating pathogen levels between sampling time periods within the first time period. The system can then repeat this process for each pathogen, in the set of pathogens, to generate a baseline pathogen profile—including a first set of pathogen profiles, each pathogen profile, in the first set of pathogen profiles, linked to a particular pathogen, in the set of pathogens—representative of changes in pathogen levels of the set of pathogens detectable in the space during the first time period. Further, the system can continue to update this baseline pathogen profile over time as the system collects additional pathogen data for this space, such as based on a second timeseries of pathogen data collected over a second time period, a third timeseries of pathogen data collected over a third time period, etc.

The system can then leverage this stored baseline pathogen profile to detect pathogen anomalies in the space. For example, the system can: access a first timeseries of pathogen data for a first pathogen, in a set of pathogens, collected during a first time period in a particular space; generate a first pathogen profile representative of changes in pathogen levels of the first pathogen during the first time period based on the first timeseries of pathogen data; access a baseline pathogen profile, for this particular space, including a preceding timeseries of pathogen data, for the first pathogen, collected during a preceding time period (e.g., prior to the first period); characterize a difference between the first pathogen profile and the baseline pathogen profile; and, in response to the difference exceeding a threshold difference, flag this first timeseries of pathogen data as a pathogen anomaly. For example, to characterize the difference between the first pathogen profile and the baseline pathogen profile, the system can: calculate an average pathogen level of the first pathogen over the first time period based on pathogen levels included in the first timeseries of pathogen data; calculate a total average pathogen level of the first pathogen over the preceding time period based on pathogen levels of the first pathogen in the baseline pathogen profile; and calculate a difference between the first average and the total average. Then, the system can: calculate a standard deviation in pathogen level for the first pathogen over the preceding time period; and, in response to the difference exceeding the standard deviation, flag the first timeseries of pathogen data as a pathogen anomaly.

Alternatively, in another example, to characterize the difference between the pathogen profile and the baseline pathogen profile, the system can: calculate a second average pathogen level of the first pathogen over a subset of the preceding time period based on pathogen levels of the first pathogen in the baseline pathogen profile recorded during the subset of the preceding time period, such as during a time period immediately preceding the first time period; and similarly characterize the difference based on a difference between the first average and the second average. Therefore, in this example, the system can compare current timeseries of pathogen data with a preceding timeseries of pathogen data (e.g., recorded in a contiguous sampling time period) stored in the baseline pathogen profile.

Therefore, the system can monitor changes in pathogen levels over time in this particular space. Additionally, the system can combine this timeseries of pathogen data with baseline (static) pathogen levels recorded for these pathogens (e.g., during an initial setup time period) to: detect anomalies in pathogen levels of pathogens; identify when changes in pathogen levels occur; and identify events and/or other environmental factors that may trigger these changes in pathogen levels. Over time, the system can continue to update the baseline pathogen profile based on additional timeseries of pathogen data from pathogen samples collected in this space.

Further, the system can leverage this baseline pathogen profile to predict current or future pathogen levels within the space. For example, during a first time period, the system can access a first timeseries of pathogen data including: a first pathogen level of a first pathogen detected in a first pathogen sample collected during a first sampling window within the first time period; a second pathogen level of a second pathogen detected in a second pathogen sample collected during a second sampling window, succeeding the first sampling window, within the first time period; and a third pathogen level of the first pathogen, detected in a third pathogen sample collected during a third sampling window succeeding the second sampling window, within the first time period. The system can then characterize a first pathogen profile of the first pathogen during the first time period based on the first pathogen level, the second pathogen level, and the third pathogen level. Then, the system can: access a baseline pathogen profile including a historical timeseries of pathogen data of the first pathogen within the space; characterize a correlation between the first pathogen profile and the baseline pathogen profile; and predict a fourth pathogen level during a fourth sampling window, succeeding the third sampling window based on the correlation.

Additionally, by leveraging a timeseries of pathogen data to characterize this baseline pathogen profile, the system can account for expected changes in pathogen levels within a space during a particular time period. For example, pathogen levels in a particular space may change frequently within a given time period of time, such as at different times of day, on different days of the week, at different occupancy levels, and at different occupancy levels within the space. For example, the system can include an air sampler installed within a shop located within a larger shopping facility (e.g., a mall). In this example, the system can detect: relatively low pathogen levels when the shop opens; detect relatively high pathogen levels when the shop is busy and full of people; and detect relatively moderate pathogen levels when the store is closing—due to the heavier traffic throughout the day. Therefore, when detecting anomalies in this shop, the system can account for these expected changes in pathogen levels throughout the day—reflected in the baseline pathogen profile for this shop.

4.3.1 Variation: Pathogen Model

In one variation, the system can develop and/or refine a space-specific pathogen model linking environmental controls and pathogen levels in this space. In particular, in this variation, the system can: track or access data streams for local conditions within the space, such as air temperature, humidity, time of day, indoor air velocity, human occupancy, etc.; and derive a pathogen model configured to predict pathogen data (e.g., pathogen levels) for the space during a particular time period as a function of such local conditions present in the space during the particular time period.

In one implementation, the system can develop this space-specific pathogen model during an initial set-up time period for a space. For example, during this set-up time period, the system can: access a first pathogen level of a particular pathogen corresponding to a first sampling time period during the set-up time period; access a first average population density for the space corresponding to the first sampling time period (e.g., recorded by a sensor installed in the space); access a second pathogen level of the particular pathogen corresponding to a second sampling time period, succeeding the first sampling time period, during the set-up time period; access a second average population density for the space corresponding to the second sampling time period; characterize a change in pathogen level based on the first pathogen level and the second pathogen level; characterize a change in population density based on the first average population density and the second average population density; and derive a pathogen model linking average population density and pathogen level of the particular pathogen in this space. The system can then leverage this pathogen model to: suggest mitigation actions relating to population density based on detected pathogen levels for this particular pathogen; and/or to predict current or future pathogen levels of this particular pathogen based on changes in population density in the space.

In one implementation, the system can leverage this pathogen model to calculate a "baseline" pathogen profile for the space during a particular time period based on environmental conditions in the space during the particular time period. The system can then compare a current pathogen profile representative of pathogen levels detected in the space during the particular time period to this calculated baseline pathogen profile to detect anomalies in pathogen levels in the space during the particular time period.

For example, the system can: access a timeseries of pathogen data—including timeseries pathogen levels of a first pathogen detected in the space—derived from a series of pathogen samples collected from an indoor environment during a first time period; interpret a pathogen profile for the first pathogen in the indoor environment during the first time period based on the timeseries of pathogen data; access a timeseries of environmental data—such as including timeseries temperature, humidity, occupancy, and/or HVAC data—recorded for the indoor environment during the first time period; access a pathogen model linking environmental data recorded for the space to baseline pathogen levels of a set of pathogens—including the first pathogen—in the indoor environment; calculate a timeseries of baseline pathogen data—including predicted or expected timeseries pathogen levels for the first pathogen in the indoor environment during the first time period—based on the timeseries of environmental data and the pathogen model; and interpret a baseline pathogen profile—representing predicted or expected changes in pathogen level for the first pathogen in the indoor environment during the first time period—based on the timeseries of baseline pathogen data.

Then, the system can characterize a difference between the (actual) pathogen profile and the baseline pathogen profile of the first pathogen during the first time period, such as by: comparing an average pathogen level to an average baseline pathogen level; comparing the difference at various timepoints; and/or calculating a correlation between the pathogen profile and the baseline pathogen profile. Finally, in response to the difference exceeding a threshold difference—such as defined for the first pathogen, calculated based on the baseline pathogen profile (e.g., a standard deviation) and/or pathogen profile, defined and/or calculated for the first pathogen given certain environmental conditions, defined for the all pathogens in the indoor environment, etc.—the system can flag this pathogen profile as corresponding to an anomaly in pathogen level for the first pathogen in the indoor environment.

In this variation, the system can develop a unique pathogen model for each environmental characteristic for a particular space. Alternatively, the system can develop a single pathogen model configured to intake all environmental controls and output a predicted pathogen level for this particular space.

4.3.2 Trend Analysis: Pathogen Profiles

In one implementation, the system can detect anomalies in pathogen levels—of a particular pathogen and/or set of pathogens in the indoor environment—based on characteristics of a (current) pathogen profile derived for the particular pathogen and/or set of pathogens in the indoor environment.

For example, the system can access a timeseries of pathogen data: derived from a series of pathogen samples collected by an air sampler, installed in an indoor environment, during a first time period; and representing levels of a set of pathogens (or any other type of microbe) in the indoor environment during the first time period. Then, for each pathogen, in the set of pathogens, the system can derive a pathogen profile (e.g., a population curve), in a set of pathogen profiles, for the pathogen based on the timeseries of pathogen data, such as based on a subset of the timeseries of pathogen data corresponding to the pathogen. The system can then characterize population growth and/or population decline (or "reduction") of the pathogen during the first time period based on the pathogen profile.

In particular, in the preceding example, the timeseries of pathogen data can include: a first pathogen level of a first pathogen, in the set of pathogens, in the indoor environment at a first time within the first time period; a first time value linked to the first pathogen level and corresponding to the first time; a second pathogen level of the first pathogen in the indoor environment at a second time succeeding the first time within the first time period; a second time value linked to the second pathogen level and corresponding to the second time; a third pathogen level of the first pathogen in the indoor environment at a third time succeeding the second time within the first time period; and a third time value linked to the third pathogen level and corresponding to the third time. The system can then derive a first pathogen profile, in the set of pathogen profiles, representing changes in population of the first pathogen in the indoor environment during the first time period. For example, the system can derive the first pathogen profile—such as represented by a curve (or "population curve") (e.g., an exponential and/or logistic curve)—by: interpolating pathogen levels of the first pathogen between the first and second time value based on the first and second pathogen level; and interpolating pathogen levels of the first pathogen between the second and third time value based on the second and third pathogen level.

In the preceding example, the system can then leverage this derived pathogen profile—representing change in population of the first pathogen over the first time period—to characterize population growth and/or decline of the first pathogen in the indoor environment during the first time period. For example, the system can estimate a first population growth rate of the first pathogen, such as based on a slope and/or pattern of the pathogen profile (or "population curve"). The system can then characterize population growth of the first pathogen during the first time period as: (relatively) slowly increasing, such as based on the pathogen profile exhibiting a positive slope and the first population growth rate falling below a threshold growth rate; (relatively) rapidly increasing, such as based on the pathogen profile exhibiting a positive slope and the first population growth rate exceeding the threshold growth rate; (relatively) slowly decreasing, such as based on the pathogen profile exhibiting a negative slope and the first population growth rate falling below the threshold growth rate; and/or (relatively) rapidly decreasing, such as based on the pathogen profile exhibiting a negative slope and the first population growth rate exceeding the threshold growth rate.

4.4 Tracking Pathogen Ratios

In one implementation, the system can compare (current) pathogen profiles derived for different pathogens detected in the indoor environment to detect anomalies in pathogen levels of these pathogens. In particular, in this implementation, the system can: derive a pathogen profile for each pathogen, in a set of pathogens, detected in the indoor environment over a particular time period; interpret a timeseries of pathogen ratios—representing ratios of pathogen levels of the set of pathogens during the particular time period—based on each of the pathogen profiles; and detect anomalies in pathogen levels based on changes in these ratios over time.

For example, the system can access a first timeseries of pathogen data derived from a series of pathogen samples collected by an air sampler, installed in the indoor environment, during a first time period and including: a first pathogen level of a first pathogen, in the set of pathogens, detected at a first time; a second pathogen level of a second pathogen, in the set of pathogens, detected at the first time; a third pathogen level of the first pathogen, detected at a second time succeeding the first time; and a fourth pathogen level of the second pathogen detected at the second time. The system can then: calculate a first ratio of the first pathogen level, of the first pathogen, to the second pathogen level, of the second pathogen, at the first time; and a second ratio of the third pathogen level, of the first pathogen, to the fourth pathogen level, of the second pathogen, at the second time.

Then, in the preceding example, in response to the first ratio exceeding the second ratio (e.g., by more than a threshold deviation), the system can flag a population of the first pathogen as: growing at a faster rate than a population of the second pathogen in the indoor environment during the first time period; and/or declining (e.g., reducing) at a slower rate than the population of the second pathogen in the indoor environment during the first time period. Alternatively, in response to the second ratio exceeding the first ratio (e.g., by more than a threshold deviation), the system can flag the population of the second pathogen as: growing at a faster rate than the population of the first pathogen in the indoor environment during the first time period; and/or declining at a slower rate than the population of the first pathogen in the indoor environment during the first time period.

Additionally and/or alternatively, in the preceding example, in response to the first ratio falling within a threshold deviation of the second ratio, the system can flag the populations of the first and second pathogens as growing and/or declining at approximately (e.g., within the threshold deviation) equivalent rates. Based on this population growth and/or decline at approximately equivalent rates, the system can leverage information regarding the first and second pathogen—such as characteristics common to these pathogens—to predict a causal pathway (e.g., an environmental condition or cause) associated with (e.g., triggering) the population growth and/or decline of the first and second pathogen. Alternatively, if each pathogen, in the set of pathogens, exhibits population growth, but the pathogen ratios exhibit little to no change over time, the system can: predict an issue with detectability and/or airflow at the air sampler; and flag the air sampler and/or environment for further investigation by a user associated with the indoor environment.

The system can then repeat this process for each pathogen, in the set of pathogens, with each other pathogen in the set of pathogens and/or with a subset of pathogens in the set of pathogens. Based on changes in these ratios over time, the system can thus delineate between expected population growth and/or changes in populations exhibited by all pathogens in the indoor environment (e.g., due to daily fluctuations in populations, due to changes in detection and/or airflow proximal the air sampler, due to changes in environmental conditions) and anomalous population growth and/or anomalous changes in populations exhibited by a particular pathogen.

5. Defined Pathogen Sets

In one implementation, the system can track microbe levels (e.g., pathogen levels, non-pathogenic microbe levels) and/or detect anomalies in microbe levels of microbes within a particular set of microbes. In particular, in this implementation, the system can track microbe levels of microbes within this defined (e.g., predefined, identified) group of microbes—such as including microbes exhibiting similar changes in microbe levels over time and/or exhibiting characteristics common to microbes in the defined group—to derive insights related to increases and/or decreases in populations of microbes in these defined groups in a particular indoor environment. For example, the system can define groups of microbes based on characteristics of these microbes such as growing and/or living conditions (e.g., temperature, humidity, location, source, food source), transfer conditions (e.g., airborne transfer, surface transfer, food consumption), response to environmental conditions (e.g., temperature, humidity, HVAC settings, chemicals and/or other disinfectants), population growth and/or reduction patterns, etc.

In one example, the system can: define a first subset of microbes, in a set of microbes, based on a common growth condition—exhibited by each microbe in the first subset of microbes—associated with presence of food and/or a transfer condition of consumption of contaminated food by humans; define a second set of microbes, in the set of microbes, based on a common growth and/or living condition—exhibited by each microbe in the second subset of microbes—associated with soil (e.g., microbes that live in soil) and/or a transfer condition of contact with surfaces containing these microbes; define a third set of microbes, in the set of microbes, based on a common response—exhibited by each microbe in the third subset of microbes—to a particular chemical (e.g., chlorine), such as population decline (e.g., due to microbe death) and/or population increase; etc.

The system can thus detect changes in populations of microbes in these defined groups of microbes over time to: identify correlations in population changes (e.g., population growth and/or decline) in microbes within a particular defined group of microbes; and predict causes of these population changes—such as due to changes in environmental conditions in the indoor environment—based on these correlations.

For example, the system can: access a timeseries of pathogen data—representing levels of a set of microbes—derived from a series of pathogen samples collected by an air sampler, installed in an indoor environment, during a first time period; and, for each microbe, in the set of microbes, derive a population curve, in a set of population curves, representing changes in population of the microbe present in the indoor environment during the first time period based on the timeseries of pathogen data. Then, for a first subset of microbes in the set of microbes, the system can characterize a first correlation—such as by calculating a correlation coefficient—between a first subset of population curves, in the set of population curves, corresponding to the first subset of microbes. The system can leverage this first correlation to interpret whether populations of microbes in the first subset of microbes exhibit (relatively) similar changes in the indoor environment during the first time period. In particular, in this example, in response to the first correlation exceeding a threshold correlation, the system can confirm correlation between the first subset of population curves and identify whether populations of microbes in the first subset of microbes are generally increasing, generally decreasing, and/or generally constant. The system can then leverage this information—represented by the first correlation—to identify and/or predict a cause (or "causal pathway") of this detected change in population of the first subset of microbes during the first time period, based on characteristics common within the first subset of microbes.

The system can therefore characterize changes in populations of these subsets of microbes over time to: derive insights related to conditions in the indoor environment; identify changes in environmental conditions in the indoor environment—such as due to a particular mitigation action executed in the indoor environment—linked to changes in populations of microbes detected over time based on characteristics common to each subset of microbes; and/or predict changes in microbe levels in the indoor environment based on these environmental conditions and characteristics of these microbes.

5.1. Causal Pathways

In one implementation, the system can predict a causal pathway for fluctuations (e.g., increases and/or decreases) in populations of groups of microbes based on characteristics common within the group of microbes. In particular, in this implementation, the system can: characterize a correlation between population curves—representing changes in populations of microbes present in the indoor environment during a particular time period—derived for a particular group of microbes (e.g., based on timeseries pathogen data collected during the particular time period); and—based on the correlation—predict a particular causal pathway (e.g., an environmental condition linked to population growth or decrease) for a change in population (e.g., population growth and/or decline) of the particular group of microbes during the particular time period.

For example, the system can: access a timeseries of pathogen data, derived from a series of pathogen samples collected by an air sampler, installed in an indoor environment, during a first time period, and representing levels of a set of microbes; and, for each microbe, in the set of microbes, derive a population curve (or "microbe profile"), in a set of population curves, representing changes in population of the microbe present in the indoor environment during the first time period based on the timeseries of pathogen data. Then, for a first subset of microbes in the set of microbes, the system can: characterize a first correlation between a first subset of population curves, in the set of population curves, corresponding to the first subset of microbes; and, based on the first correlation, predict a first causal pathway for an increase in populations of the first subset of microbes during the first time period based on characteristics common within the first subset of microbes. In particular, in one example, the system can predict the first causal pathway based on the first correlation exceeding a threshold correlation, thereby indicating presence of a correlation between the first subset of correlation curves. Alternatively, in this example, in response to the first causal pathway falling below the threshold correlation, the system can dissociate changes in populations of microbes in the second subset of microbes from the first causal pathway.

The system can thus: predict the first causal pathway—associated with characteristics (e.g., growth, living, and/or transfer conditions, response to stimuli and/or environmental conditions) common to the first subset of microbes—responsive to detecting increases (or decreases) in populations of the first subset of microbes; and/or eliminate the first causal pathway as associated with increases (or decreases) in populations of the set of microbes based on absence of a correlation between the first subset of correlation curves.

In the preceding implementation, the system can predict a particular causal pathway—and/or eliminate a particular causal pathway—based on behavior (e.g., population growth or decline) of multiple groups of microbes and characteristics common to microbes in these groups.

For example, the system can define a first subset of microbes, in a set of microbes, including a first microbe and a second microbe; and define a second subset of microbes, in the set of microbes, including the first microbe, including a third microbe, and excluding the second microbe. Then, for each microbe in the set of microbes, the system can derive a population curve, in a set of population curves, representing changes in population of the microbe present in the indoor environment during a particular time period based on timeseries pathogen data collected during the particular time period. Then, the system can: characterize a first correlation between a first subset of population curves, in the set of population curves, corresponding to the first subset of microbes; and characterize a second correlation between a second subset of population curves, in the set of population curves, corresponding to the second subset of microbes. In this example, in response to the first correlation exceeding a threshold correlation and the second correlation falling below the threshold correlation, the system can: predict a first causal pathway for an increase in populations of the first subset of microbes during the particular time period based on characteristics common within the first subset of microbes; and, dissociate an increase in populations of the second subset of microbes during the first time period from a second causal pathway.

Therefore, rather than predict a particular causal pathway based on an increase in population of a particular microbe and/or each microbe, in a set of microbes, individually, the system can analyze changes in populations of subsets of microbes to: isolate a characteristic or set of characteristics common to the subset of microbes; and more accurately predict a causal pathway linked to population growth of these subsets of microbes based on shared or common characteristics of microbes in these subsets of microbes.

For example, in response to detecting an increase in populations of a first subset of microbes—associated with foodborne transfer—the system can predict a first causal pathway corresponding to presence of contaminated food, food waste, and/or improper food storage and/or handling. In another example, in response to detecting an increase in populations of a second subset of microbes—associated with airborne transfer—the system can predict a second causal pathway corresponding to increased human occupancy and/ or changes in air filtration in the indoor environment. In yet another example, in response to detecting an increase in populations of a third subset of microbes —associated with soil—the system can predict a third causal pathway corresponding to increased soil and/or microbe introduction into the indoor environment (e.g., due to tracking of soil on shoes worn into the indoor environment from outside). In this example, the system can therefore: link detection of increases in population of the first subset of microbes to presence of contaminated food, food waste, and/or improper food storage and/or handling; link detection of increases in population of the second subset of microbes to increased human occupancy and/or changes in air filtration in the indoor environment; and link detection of increases in population of the first subset of microbes to increased soil and/or microbe introduction into the indoor environment. Therefore, based on the predicted causal pathway, the system can select a mitigation action configured to suppress or inhibit this causal pathway in the indoor environment, thereby inhibiting population growth of the corresponding subset of microbes.

Further, in this implementation, by analyzing microbe population growth in defined groups rather than individually, the system can predict a particular causal pathway from a set of causal pathways—such as a first, second, third, etc. causal pathway—associated with a single microbe.

For example, for each microbe, in a set of microbes, the system can derive a population curve, in a set of population curves, representing changes in population of the microbe present in the indoor environment during a particular time period (e.g., based on timeseries of pathogen data). The system can then define a first subset of microbes, in a set of microbes, including: a first microbe associated with the first causal pathway and a second causal pathway predicted to increase population of the first microbe; and a second microbe associated with the first causal pathway and a third causal pathway predicted to increase population of the second microbe. The system can further define a second subset of microbes, in the set of microbes, and including: the first microbe; and a third microbe associated with the second causal pathway and a fourth causal pathway predicted to increase population of the third microbe.

Then, the system can: characterize a first correlation between a first subset of population curves, in the set of population curves, corresponding to the first subset of microbes; and characterize a second correlation between a second subset of population curves, in the set of population curves, corresponding to the second subset of microbes. Finally, the system can: predict the first causal pathway, in place of the second causal pathway and the third causal pathway, for the increase in populations of the first subset of microbes during the particular time period—based on characteristics common within the first microbe and the second microbe—in response to the first correlation exceeding a threshold correlation; or predict the second causal pathway, in place of the first causal pathway, the third causal pathway, and the fourth causal pathway, for an increase in populations of the second subset of microbes during the particular time period—based on characteristics common within the first microbe and the third microbe—in response to the second correlation exceeding the threshold correlation.

6. Mitigation Actions

The system can identify and suggest mitigation actions configured to limit pathogen anomalies and/or reduce pathogen levels in a particular space. For example, the system can suggest mitigation actions configured to control and/or adjust various environmental factors in the space such as: air dilution (e.g., increased ventilation in the space); disinfection (e.g., applying air and/or surface disinfectants in the space); filtration; occupancy (e.g., increasing and/or monitoring space between occupants, metering occupants in the space); etc.

In one implementation, the system can leverage a timeseries of pathogen data, collected during a setup time period, to select a mitigation action configured to limit pathogen anomalies and/or reduce pathogen levels (e.g., over time) in a particular space over time.

Additionally and/or alternatively, in another implementation, the system can identify and suggest particular mitigation actions responsive to detecting a pathogen anomaly in the space. In particular, in this implementation, in response to detecting a pathogen anomaly linked to a particular pathogen in the space, the system can: identify a first mitigation action, in a set of mitigation actions, configured to reduce a pathogen level of the particular pathogen to below a threshold pathogen level (e.g., within a particular duration); generate a prompt to implement the first mitigation action (e.g., within a particular time period of time or at a particular frequency); and transmit this prompt to a user (e.g., an administrator, a manager, an employee) associated with the particular space for implementation.

In one implementation, the system can initially select a generic mitigation action for the space based on the set of pathogens or pathogen level(s) detected. Over time (e.g., over a next sampling time period or over a next set of sampling time periods), the system can continue monitoring this set of pathogens to confirm, modify, and/or refine the mitigation action to converge on a space-specific mitigation action. In another implementation, the system can select a mitigation action for the space based on the pathogen profile of this space. For example, in response to detecting a pathogen anomaly (e.g., corresponding to a particular pathogen) in a space, the system can: access a pathogen profile of the space; access a mitigation model linking pathogen profiles (e.g., types, magnitudes, and changes in pathogens over time) to specific mitigation actions; and identify a particular mitigation action best matched to the space based on the pathogen anomaly, the pathogen profile and the mitigation model.

6.1 Mitigation Action Linked to Causal Pathway

Additionally and/or alternatively, in another implementation, the system can select a mitigation action configured to suppress and/or inhibit a particular causal pathway identified (e.g., predicted) for an increase in population of a particular pathogen and/or group of pathogens (or any other type of microbe or group of microbes).

For example, the system can define: a first subset of microbes (e.g., pathogens) including a first microbe—associated with a first causal pathway (e.g., change in chemical disinfectant presence in the environment) and a second causal pathway (e.g., change in food cleanliness in the environment)—and a second microbe associated with the first causal pathway (e.g., change in chemical disinfectant presence in the environment); and a second subset of microbes (e.g., pathogens) including the first microbe and a third microbe associated with the second causal pathway (e.g., change in food cleanliness in the environment). The system can then: access a timeseries of pathogen data—representing levels of a set of pathogens—derived from a series of pathogen samples collected by an air sampler, installed in an indoor environment, during a first time period; derive a first population curve, in a set of population curves, representing changes in population of the first microbe present in the indoor environment during the first time period, based on the timeseries of pathogen data; derive a second population curve, in the set of population curves, representing changes in population of the second microbe present in the indoor environment during the first time period, based on the timeseries of pathogen data; and derive a third population curve, in the set of population curves, representing changes in population of the third microbe present in the indoor environment during the first time period, based on the timeseries of pathogen data.

Then, in the preceding example, in response to the first correlation exceeding a threshold correlation—thereby indicating relatively high correlation between the first and second population curves of the first and second pathogen—and corresponding to an increase in population of the first and second microbes (i.e., the first subset of microbes)—and/or in response to the second correlation falling below the threshold correlation, thereby indicating relatively low correlation between the first and third population curves of the first and third pathogen—the system can predict the first causal pathway—associated with the first and second microbes—for an increase in populations of the first subset of microbes during the first time period. Then, in response to predicting the first causal pathway, the system can select a mitigation action, in a set of mitigation actions, linked to suppression of the first mitigation action.

For example, in response to predicting the first causal pathway corresponding to a change in presence of a chemical disinfectant (e.g., chlorine) in the environment, the system can select a first mitigation action—such as including application of a particular dosage (e.g., an amount and/or frequency) of application of a particular chemical disinfectant in regions of the indoor environment—configured to suppress the first causal pathway. Alternatively, in another example, in response to predicting a second causal pathway corresponding to presence of food in the environment, the system can select a second mitigation action including a cleaning regimen—such as including weekly emptying of contents in a shared food storage space (e.g., a refrigerator) and/or daily disinfecting of surfaces in a region of the environment associated with food consumption (e.g., a kitchen, a break room)—configured to suppress the second causal pathway. Alternatively, in yet another example, in response to predicting a third causal pathway corresponding to presence of soil microbes (e.g., pathogenic soil microbes, non-pathogenic soil microbes) in the environment, the system can select a third mitigation action—such as including daily cleaning of floors in the environment during a particular season and/or placement of mats (e.g., for removal of soil from shoes) in an entryway to the indoor environment—configured to suppress the third causal pathway.

The system can therefore selectively suggest mitigation actions—configured to regulate microbe levels (e.g., pathogen levels) within the indoor environment—based on correlations between changes in pathogen levels of different microbes exhibiting similar or shared characteristics.

6.2 Intervention Effectiveness

In one implementation, upon implementation of a particular mitigation action in the space, the system can monitor whether this particular mitigation action is effective (e.g., for reducing pathogen levels) in the space based on pathogen samples collected during and/or after execution of the mitigation action.

For example, at a first time, in response to detecting a pathogen anomaly in a cafeteria of a school, the system can: generate a prompt to implement a first mitigation action specifying application of a particular type of disinfectant to surfaces (e.g., table surfaces) in the cafeteria twice per day;

and transmit this prompt to a worker (e.g., a lead custodian, an administrator) associated with the school. The system can then transmit a request to the worker to confirm completion (e.g., via the native application) of this first mitigation action (e.g., applying disinfectant to surfaces in the cafeteria twice per day) each day during a test time period. Then, at a second time succeeding the first time (e.g., one week later, one month later), the system can: access a timeseries of pathogen data corresponding to pathogen samples collected during the test time period; characterize a pathogen profile for the cafeteria during the test time period based on the timeseries of pathogen data; and, in response to the pathogen profile falling within a threshold deviation of a target pathogen profile (e.g., based on the baseline pathogen profile, corresponding to healthy pathogen levels within this space) for this space, confirm efficacy of the first mitigation action in this space. Alternatively, in response to the pathogen trend falling outside of the deviation of the target pathogen profile, the system can suggest a modification (e.g., increase in frequency) to the first mitigation action and/or suggest a second mitigation action in replacement of the first mitigation action.

In one example, to verify efficacy of a particular mitigation action, the system can compare a current pathogen profile—derived from a series of pathogen samples collected by the air sampler, installed in the indoor environment, during a time period succeeding execution of the particular mitigation action—to a baseline pathogen profile derived for the indoor environment. In particular, in this example, in response to confirming execution of a mitigation action—configured to reduce populations and/or population growth of a first pathogen, in a set of pathogens, in the indoor environment—at a first time, the system can: access a timeseries of pathogen data for the first pathogen and derived from a series of pathogen samples collected from the indoor environment during a time period succeeding the second time; characterize a pathogen profile for the indoor environment during the time period based on the timeseries of pathogen data; and, in response to the difference falling below a threshold difference, confirm efficacy of the first mitigation action.

Additionally and/or alternatively, in another example, the system can compare the current pathogen profile to a preceding pathogen profile—such as corresponding to an anomaly in pathogen level for the first pathogen—derived from an initial series of pathogen samples collected by the air sampler during an initial time period preceding execution of the particular mitigation action. In particular, in this example, the system can: characterize a difference (e.g., a reduction) between the current pathogen profile and the preceding pathogen profile; and, in response to the difference exceeding the threshold difference—thereby indicating a reduction in growth and/or population of the first pathogen—confirm efficacy of the first mitigation action. Alternatively, in this example, in response to the difference falling below the threshold difference, the system can select a second mitigation action—in replacement of the first mitigation action—configured to reduce pathogen levels of the first pathogen in the indoor environment.

Additionally, in one variation, the system can confirm whether a suggested mitigation action for a space was completed and leverage this information to inform deployment of various mitigation actions in this space in the future. In particular, in the preceding example, the system can prompt the worker associated with the cafeteria to confirm completion of application of the disinfectant to surfaces in the cafeteria each day. Therefore, if the system does not receive this confirmation from the worker, the system can: adjust the target pathogen profile for this test time period based on an extent to which the worker confirmed implementation of the first mitigation action; suggest a replacement mitigation action that the worker may be more likely to implement; and/or transmit a notification (or series of notifications) to the worker as a reminder to implement the first mitigation action.

If a particular mitigation action is highly successful at mitigating pathogen anomalies (e.g., for a particular pathogen) in the space (e.g., based on recorded pathogen data), the system can assign a high rank to this particular mitigation action for this space. Alternatively, if a particular mitigation action is less successful at mitigating pathogen anomalies in the space, the system can assign a low rank to this particular mitigation action. Therefore, over time, the system can learn which mitigation actions work best for mitigating and/or limiting pathogen anomalies in this space. Further, by suggesting these mitigation actions to users associated with the space, the system enables these users to better prepare for and/or better react to pathogen anomalies in this space in the future.

6.2.1 Intervention Effectiveness: Regulating Causal Pathways

In one implementation, the system can characterize effectiveness of a particular mitigation action based on a magnitude of suppression of a particular causal pathway linked to the mitigation action.

In particular, in this implementation, the system can: derive a first set of populations curves—for a set of microbes (e.g., pathogens) detected in an indoor environment—representing changes in populations of the set of microbes present in the indoor environment, during a first time period, based on a first timeseries of pathogen data derived from a first series of pathogen samples collected during the first time period; based on a first correlation between a first subset of population curves, in the first set of population curves, corresponding to a first subset of microbes, in the set of microbes, predict a first casual pathway for an increase in populations of the first subset of microbes, during the first time period, based on characteristics (e.g., growth conditions, living conditions, life-threatening conditions, food source) common within the first subset of microbes; and transmit a prompt to execute a first mitigation action—linked to suppression of the first causal pathway—to a user associated with the indoor environment. Later—such as in response to confirming execution of the first mitigation action—the system can: access a second timeseries of pathogen data—representing levels of the set of microbes—derived from a second series of pathogen samples collected by the air sampler during a second time period succeeding the first time period; derive a second set of population curves—for the set of microbes detected in the indoor environment—representing changes in population of the set of microbes during the second time period based on the second timeseries of pathogen data.

Then, in the preceding example, the system can: characterize a difference between the first subset of population curves and a second subset of population curves, in the second set of population curves, corresponding to the first subset of microbes; and, based on the difference, confirm efficacy of the first mitigation action in suppressing the first causal pathway in the indoor environment. For example, the system can confirm efficacy of the first mitigation action based on the difference (e.g., a magnitude of population reduction) exceeding a threshold difference (e.g., a threshold reduction in population). Additionally and/or alternatively, in another example, for each microbe in the first subset of microbes, the system can characterize a microbe difference, in a set of microbe differences, between a first population curve, in the first subset of population curves, and a second population curve, in the second subset of population curves, the first population curve and the second population curve corresponding to the microbe; characterize a total difference based on the set of microbe differences; for each microbe, in the first subset of microbes, in response to the microbe difference exceeding a threshold difference defined for the microbe, confirm efficacy of the first mitigation action for suppressing population growth of the microbe; and, based on the total difference, confirm efficacy of the first mitigation action for suppressing the first casual pathway.

The system can therefore confirm efficacy of the first mitigation action in both suppressing population growth of particular microbe (e.g., pathogen)—such as based on changes in population of this particular microbe detected after execution of the mitigation action—and/or suppressing a particular causal pathway associated with increase and/or decrease in population of a particular group of microbes (e.g., pathogens), such as based on changes in populations of this particular group of microbes detected after execution of the mitigation action.

Additionally, in another implementation, the system can confirm completion of a particular mitigation action based on detecting suppression and/or activation of a particular causal pathway linked to the mitigation action.

For example, at a first time, the system can prompt a user to execute a mitigation action—corresponding to application of a particular dosage of a particular chemical disinfectant—in regions of an indoor environment. Later, the system can: access a timeseries of pathogen data—representing levels of a set of pathogens over time—derived from a series of pathogen samples collected by an air sampler, installed in the indoor environment, during a first time period succeeding the first time; and, for each pathogen, in the set of pathogens, derive a population curve, in a set of population curves, representing changes in population of the pathogen present in the indoor environment during the first time period based on the timeseries of pathogen data. Then, for a first subset of pathogens in the set of pathogens—each pathogen in the first subset of pathogens exhibiting a known response (e.g., population decline due to pathogen death) responsive to exposure (e.g., above a threshold magnitude) to the particular chemical disinfectant—the system can: characterize a correlation between a first subset of population curves, in the set of population curves, corresponding to the first subset of pathogens; and, in response to the correlation exceeding a threshold correlation and indicating population decline (e.g., a reduction in population exceeding a threshold reduction) of the first subset of pathogens, confirming execution of the first mitigation action in the indoor environment.

The system can therefore leverage identification of a causal pathway—associated with population growth and/or population decline of a particular pathogen and/or group of pathogens—to confirm and/or disconfirm execution of a particular mitigation action linked to this causal pathway.

6.2.2 Efficacy Model

In one implementation, the system can derive an efficacy model configured to represent and/or predict changes in efficacy of a particular mitigation action in regulating populations of a particular microbe and/or group of microbes—such as by suppressing a particular causal pathway linked to the particular microbe and/or group of microbes—over time.

For example, the system can: transmit a prompt to execute a first mitigation action—linked to suppression of a first causal pathway in an indoor environment—to a user associated with the indoor environment at a first time; at a second time succeeding the first time, receive confirmation of execution of the first mitigation action in the indoor environment from the user; access a timeseries of pathogen data—representing levels of a set of microbes—derived from a series of pathogen samples collected by an air sampler during a time period succeeding the second time. Then, for each microbe, in the set of microbes, the system can derive a population curve, in a set of population curves, representing changes in population of the microbe, present in the indoor environment during the time period, based on the timeseries of pathogen data. The system can then leverage the set of population curves to derive an efficacy model representing change in efficacy of the first mitigation action in regulating populations of the set of microbes over time.

The system can derive this efficacy model for a particular group of microbes associated with the first causal pathway, for a particular pathogen associated with the first causal pathway, and/or for all pathogens in the set of pathogens. Further, the system can leverage the efficacy model to identify groups of pathogens, in the set of pathogens, exhibiting similar temporal responses (e.g., population changes) to execution of the first mitigation action in the indoor environment.

The system can therefore represent and/or predict efficacy of a particular mitigation action—in regulating a particular pathogen or group of pathogens in the indoor environment—as a function of time (e.g., time passed after execution of the mitigation action). Therefore, based on this efficacy model, the system can leverage timeseries pathogen data to extrapolate: a particular (future) time corresponding to a microbe level—for a particular microbe and/or group of microbes—below a threshold microbe level; a particular (future) time corresponding to a microbe level—for a particular microbe and/or group of microbes—exceeding the threshold microbe level; a particular (future) time corresponding to null efficacy of the mitigation action and/or corresponding to execution of a second instance of the mitigation action; a particular (future) time corresponding to maximum efficacy of the mitigation action; etc.

6.3 Interventions: Environmental Controls

The system can identify environmental controls (e.g., environmental conditions)—such as air temperature, air pressure, occupancy levels (e.g., occupant density, number of occupants), HVAC settings, air filtration rates, etc.—that may be indicative of pathogen levels or anomalies in the space. The system can then leverage these environmental controls to: predict current or future pathogen levels or anomalies in the space; and to suggest particular mitigation actions for the space based on these environmental controls. For example, in response to detecting a pathogen anomaly for a pathogen in a space, the system can: access a current population density level associated with this pathogen anomaly; and suggest a maximum population density level less than the current population density level. Further, the system can then associate the current population density level with the pathogen anomaly and store this information fur informing future selection of mitigation actions in this space.

In one implementation, the system can prompt a user associated with the space to periodically provide (e.g., via the native application) environmental controls corresponding to pathogen anomalies. For example, in response to detecting a pathogen anomaly in a space, the system can prompt a user associated with the space to complete a report detailing environmental controls associated with the pathogen anomaly, such as: a quantity of people that entered the space during a sampling time period corresponding to the pathogen anomaly; a maximum quantity of people that occupied the space concurrently during the sampling time period; whether a window in the space was open during the sampling time period; whether cleaning protocols (i.e., mitigation actions) were implemented; which cleaning protocols were implemented; etc.

In another implementation, the system can be configured to record environmental data corresponding to the space during collection of pathogen samples within the space. The system can then evaluate whether a set of environmental controls in place (e.g., during collection of a pathogen sample) are effective at preventing increases in pathogen levels and/or at reducing pathogen levels. For example, during a first sampling window, the system can: trigger collection of a first pathogen sample at the air sampler installed in a space; access a set of environmental sensors— such as installed within a smart HVAC system—installed in the space; and record a first set of environmental data as read by the set of environmental sensors, such as a current airflow rate, a current air filtration rate, a current occupancy in the space, a current population density, etc. The system can then automatically link this first set of environmental data to the first pathogen level collected during the first sampling window. Then, during a second sampling window, the system can: trigger collection of a second pathogen sample at the air sampler; and access the set of environmental sensors to record a second set of environmental data as read by the set of environmental sensors. In response to detecting an increase in pathogen level of a particular pathogen between the first sampling window and the second sampling window, the system can leverage the first and second sets of environmental data to identify changes to the set of environmental controls, which may be linked to the increase in pathogen level of the particular pathogen. In this example, in response to detecting a decrease in airflow rate in the space between the first sampling window and the second sampling window, the system can suggest increasing the airflow rate in the space to mitigate the increase in pathogen level. Alternatively, the system can be configured to wirelessly communicate with the smart HVAC system to automatically increase the airflow rate.

7. Variation: Health Scores

In one variation, the system can leverage the pathogen profile for the space to calculate a health score for the space (e.g., at a particular time or over a particular time period of time).

For example, the air sampler can be installed in a restaurant. Each week (e.g., after the weekend), the system can calculate a health score for the restaurant based on pathogen levels of various pathogens in the restaurant throughout the week. In particular, during a first period of time, the system can: trigger collection of a first pathogen sample during a first sampling window (e.g., 24 hour, 48 hours, 72 hours) within the first period of time; trigger collection of a second pathogen sample during a second sampling window succeeding the first sampling window within the first period of time; and trigger collection of a third pathogen sample during a third sampling window succeeding the second sampling window within the first period of time. The system can then: access a first set of pathogen levels, corresponding to a set of pathogens, detected in the first pathogen sample; and access a set of baseline pathogen levels stored for the set of pathogens in this restaurant. The system can then calculate a first score for each pathogen, in the set of pathogens, to calculate a first set of pathogen scores, based on the first set of pathogen levels and the set of target pathogen levels. The system can repeat this process to calculate a second set of pathogen scores and a third set of pathogen scores corresponding to the second and third sampling windows. The system can then compile the first, second, and third sets of pathogen scores to calculate a total pathogen score for the restaurant across the first, second, and third sampling windows. In this example, the system can then wirelessly share this total pathogen score with a user(s) associated with the restaurant, such as a manager of the restaurant or a health inspection worker assigned to this restaurant.

Alternatively, in the preceding example, the system can: access a first set of pathogen levels, corresponding to a set of pathogens, detected in the first pathogen sample; access a second set of pathogen levels, corresponding to the set of pathogens, detected in the second pathogen sample; and access a third set of pathogen levels, corresponding to the set of pathogens, detected in the third pathogen sample. Then, for a first pathogen, in the set of pathogens, the system can: access a first pathogen level, in the first set of pathogen levels, corresponding to the first pathogen; access a second pathogen level, in the second set of pathogen levels, corresponding to the first pathogen; access a second pathogen level, in the third set of pathogen levels, corresponding to the first pathogen; and characterize a first pathogen profile for the first pathogen based on the first pathogen level, the second pathogen level, and the third pathogen level, the first pathogen profile representative of changes in pathogen level of the first pathogen level over time (e.g., from the first sampling window through the third sampling window). The system can then: access a first baseline pathogen profile corresponding to the first pathogen in this restaurant; characterize a difference between the first pathogen profile and the first baseline pathogen profile; and, based on the difference, calculate a first health score for the first pathogen during the first period of time. The system can then repeat this process for each pathogen, in the set of pathogens, to: characterize a first set of differences between measured pathogen profiles and baseline pathogen profiles of these pathogens; and, based on the set of differences, calculate a first set of health scores corresponding to the set of pathogens during the first period of time. Additionally and/or alternatively, the system can calculate a total health score corresponding to the first set of pathogens based on the first set of differences or the first set of health scores.

The system and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method comprising:
accessing a timeseries of pathogen data:
   derived from a series of pathogen samples collected by an air sampler, installed in an indoor environment, during a first time period; and
   representing levels of a set of microbes;
for each microbe, in the set of microbes, deriving a population curve, in a set of population curves, representing changes in population of the microbe present in the indoor environment during the first time period based on the timeseries of pathogen data; and
for a first subset of microbes in the set of microbes:
   characterizing a first correlation between a first subset of population curves, in the set of population curves, corresponding to the first subset of microbes;
   based on the first correlation, predicting a first causal pathway for an increase in populations of the first subset of microbes during the first time period based on characteristics common within the first subset of microbes;
   identifying a first mitigation action, in a set of mitigation actions, linked to suppression of the first causal pathway;
   generating a prompt to execute the first mitigation action in the indoor environment; and
   transmitting the prompt to a user associated with the indoor environment.

2. The method of claim 1, further comprising:
defining the first subset of microbes comprising a first microbe and a second microbe;
defining a second subset of microbes comprising:
   the first microbe and a third microbe; and
   excluding the second microbe;
characterizing a second correlation between a second subset of population curves, in the set of population curves, corresponding to the second subset of microbes; and
based on the second correlation, dissociating an increase in populations of the second subset of microbes during the first time period from a second causal pathway.

3. The method of claim 1:
further comprising defining the first subset of microbes comprising:
   a first microbe associated with the first causal pathway and a second causal pathway predicted to increase population of the first microbe; and
   a second microbe associated with the first causal pathway and a third causal pathway predicted to increase population of the first microbe; and
wherein predicting the first causal pathway for the increase in populations of the first subset of microbes comprises, predicting the first causal pathway, in place of the second causal pathway and the third causal pathway, for the increase in populations of the first subset of microbes during the first time period in response to the first correlation exceeding a threshold correlation.

4. The method of claim 3, further comprising:
accessing a second timeseries of pathogen data:
   derived from a second series of pathogen samples collected by the air sampler during a second time period; and
   representing levels of the set of microbes;
for each microbe, in the set of microbes, deriving a second population curve, in a second set of population curves, representing changes in population of the microbe present in the indoor environment during the second period based on the second timeseries of pathogen data;
defining a second subset of microbes, in the set of microbes, comprising:
   the first microbe; and
   a third microbe associated with the second causal pathway and a fourth causal pathway predicted to increase population of the first microbe; and
for the second subset of microbes:
   characterizing a second correlation between a second subset of population curves, in the set of population curves, corresponding to the second subset of microbes;
   in response to the second correlation exceeding the threshold correlation, predicting the second causal pathway, in place of the first causal pathway, the third causal pathway, and the fourth causal pathway, for an increase in populations of the second subset of microbes during the second time period based on characteristics common within the first microbe and the third microbe;
   identifying a second mitigation action, in the set of mitigation actions, linked to suppression of the second causal pathway;
   generating a second prompt to execute the second mitigation action in the indoor environment; and
   transmitting the second prompt to the user.

5. The method of claim 1:
wherein predicting the first causal pathway based on characteristics common within the first subset of microbes comprises:
   for each microbe, in the set of microbes, accessing a set of characteristics of the microbe;
   identifying a subset of characteristics common within each set of characteristics of each microbe; and
   in response to the subset of characteristics comprising a first growth condition linked to food, predicting a food-based causal pathway associated with presence of contaminated food in the indoor environment;
wherein identifying the first mitigation action linked to suppression of the first causal pathway comprises, in response to predicting the food-based causal pathway, identifying a food-based mitigation action linked to suppression of the food-based causal pathway, the food-based mitigation action comprising a cleaning regimen configured to suppress the food-based causal pathway; and
wherein generating the prompt to execute the first mitigation action in the indoor environment comprises, in response to identifying the food-based mitigation action, generating the prompt to execute the cleaning regimen in a set of regions of the indoor environment associated with food storage.

6. The method of claim 5:
wherein predicting the first causal pathway based on characteristics common within the first subset of microbes comprises, in response to the set of characteristics corresponding to a second growth condition linked to soil, predicting a soil-based causal pathway associated with presence of soil in the indoor environment;

wherein identifying the first mitigation action linked to suppression of the first causal pathway further comprises, in response to predicting the soil-based causal pathway, identifying a soil-based mitigation action linked to suppression of the soil-based causal pathway, the soil-based mitigation action comprising placement of a set of mats configured to limit soil transfer onto floors throughout the indoor environment; and wherein generating the prompt to execute the first mitigation action in the indoor environment further comprises, in response to identifying the soil-based mitigation action, generating the prompt to locate the set of mats in a set of entryways of the indoor environment.

7. The method of claim 1:

wherein predicting the first causal pathway based on characteristics common within the first subset of microbes comprises:

for each microbe, in the set of microbes, accessing a set of characteristics of the microbe;

identifying a subset of characteristics common within each set of characteristics of each microbe; and in response to the subset of characteristics comprising a first transfer condition associated with airborne transfer, predicting an occupancy-based causal pathway associated with human occupancy levels and linked to the first transfer condition;

wherein identifying the first mitigation action linked to suppression of the first causal pathway comprises, in response to predicting the occupancy-based causal pathway, identifying an occupancy-based mitigation action linked to suppression of the occupancy-based causal pathway, the occupancy-based mitigation action comprising implementation of a threshold human occupancy density in the indoor environment; and wherein generating the prompt to execute the first mitigation action in the indoor environment comprises, in response to identifying the occupancy-based mitigation action, generating the prompt to regulate human occupancy density, in the indoor environment, below the threshold human occupancy density.

8. The method of claim 1, further comprising:

accessing a second timeseries of pathogen data:

derived from a second series of pathogen samples collected by the air sampler during a second time period succeeding the first time period; and representing levels of the set of microbes;

for each microbe, in the set of microbes, deriving a second population curve, in a second set of population curves, representing changes in population of the microbe present in the indoor environment during the second period based on the second timeseries of pathogen data; and for the first subset of microbes:

characterizing a difference between the first subset of population curves and a second subset of population curves, in the second set of population curves, corresponding to the first subset of microbes; and based on the difference, confirming efficacy of the first mitigation action.

9. The method of claim 8:

wherein characterizing the difference between the first subset of population curves and the second subset of population curves comprises:

for each microbe in the first subset of microbes, characterizing a microbe difference, in a set of microbe differences, between a first population curve, in the first subset of population curves, and a second population curve, in the second subset of population curves, the first population curve and the second population curve corresponding to the microbe; and characterizing a total difference based on the set of microbe differences; and wherein confirming efficacy of the first mitigation action based on the difference comprises:

for each microbe, in the first subset of microbes, in response to the microbe difference exceeding a threshold difference defined for the microbe, confirming efficacy of the first mitigation action for suppressing population growth of the microbe; and based on the total difference, confirming efficacy of the first mitigation action for suppressing the first causal pathway.

10. The method of claim 1 further comprising:

accessing a second timeseries of pathogen data:

derived from a second series of pathogen samples collected by the air sampler during a second time period succeeding the first time period; and representing levels of the set of microbes;

for each microbe, in the set of microbes, deriving a second population curve, in a second set of population curves, representing changes in population of the microbe present in the indoor environment during the second period based on the second timeseries of pathogen data; and for each microbe, in a second subset of microbes in the set of microbes and excluding microbes in the first subset of microbes:

characterizing a difference, in a set of differences, between the first population curve, representing changes in population of the microbe present in the indoor environment during the first time period, and the second population curve, representing changes in population of the microbe present in the indoor environment during the first time period; and in response to the difference exceeding a threshold difference defined for the microbe, associating the microbe with the first causal pathway.

11. The method of claim 1:

wherein transmitting the prompt to the user comprises transmitting the prompt to the user at a first time succeeding the first time period; and further comprising:

receiving confirmation of execution of the first mitigation action in the indoor environment from the user at a second time succeeding the first time;

accessing a second timeseries of pathogen data:

derived from a second series of pathogen samples collected by the air sampler during a second time period succeeding the second time; and representing levels of the set of microbes;

for each microbe, in the set of microbes, deriving a second population curve, in a second set of population curves, representing changes in population of the microbe present in the indoor environment during the second time period based on the second timeseries of pathogen data;

based on the second set of population curves, deriving an efficacy model representing change in efficacy of the first mitigation action in regulating populations of the first subset of microbes over time; and for a first microbe, in the first subset of microbes, predicting a microbe level, of the first microbe, falling below a threshold microbe level at a third time, succeeding the second time period, based on a current microbe level of the first microbe and the efficacy model.

12. A method comprising:

accessing a first timeseries of pathogen data for a first pathogen, in a set of pathogens, and derived from a series of pathogen samples collected during a first time period by an air sampler installed in an indoor environment;

characterizing a first pathogen profile, in a first set of pathogen profiles, of the indoor environment during the first time period based on the first timeseries of pathogen data, the first pathogen profile representative of changes in pathogen level of the first pathogen in the indoor environment during the first time period;

accessing a baseline pathogen profile of the indoor environment, the baseline pathogen profile representative of changes in pathogen levels of the set of pathogens during an initial time period preceding the first time period;

characterizing a first difference between the first pathogen profile and the baseline pathogen profile; and in response to the first difference exceeding a threshold difference:

selecting a first mitigation action, in a set of mitigation actions, configured to reduce pathogen levels of the first pathogen, based on the first difference;

generating a prompt to execute the first mitigation action in the indoor environment; and transmitting the prompt to a user associated with the indoor environment.

13. The method of claim 12:

wherein accessing the first timeseries of pathogen data for the first pathogen and derived from the series of pathogen samples collected from the indoor environment comprises accessing the first timeseries of pathogen data comprising:

a first pathogen level of the first pathogen detected in a first pathogen sample, in the series of pathogen samples, collected from the indoor environment during a first sampling period within the first time period; and a second pathogen level of the first pathogen detected in a second pathogen sample, in the series of pathogen samples, collected from the indoor environment during a second sampling period, preceding the first sampling period, within the first time period; and wherein characterizing the first difference between the first pathogen profile and the baseline pathogen profile comprises:

calculating an average pathogen level of the first pathogen during the first time period based on the first pathogen level and the second pathogen level;

accessing an average baseline pathogen level of the first pathogen during the initial time period and defined by the baseline pathogen profile; and calculating a first deviation of the average pathogen level from the average baseline pathogen level.

14. The method of claim 13:

wherein accessing the baseline pathogen profile of the indoor environment comprises accessing the baseline pathogen profile of the indoor environment comprising an initial timeseries of pathogen data for the first pathogen and derived from an initial series of pathogen samples collected from the indoor environment during the initial time period;

wherein accessing the average baseline pathogen level of the first pathogen during the initial time period and defined by the baseline pathogen profile comprises calculating the average baseline pathogen level of the first pathogen during the initial time period based on the initial timeseries of pathogen data; and wherein selecting the first mitigation action in response to the first difference exceeding the threshold difference comprises:

calculating a standard deviation in pathogen level of the first pathogen during the initial time period from the average baseline pathogen level based on the initial timeseries of pathogen data;

defining the threshold difference as the standard deviation; and in response to the deviation exceeding the standard deviation, selecting the first mitigation action.

15. The method of claim 12:

wherein accessing the first timeseries of pathogen data for the first pathogen and derived from the series of pathogen samples collected from the indoor environment during the first time period comprises accessing the first timeseries of pathogen data comprising a first pathogen level of the first pathogen and derived from a first pathogen sample, in the series of pathogen samples, collected from the indoor environment during a first sampling period within the first time period; and further comprising, during the first time period, in response to the first pathogen level exceeding a threshold pathogen level defined for the first pathogen in the indoor environment:

generating a notification indicating detection of presence of the first pathogen in the indoor environment; and transmitting the notification to a user associated with the environment.

16. The method of claim 12:

wherein accessing the first timeseries of pathogen data for the first pathogen and derived from the series of pathogen samples collected from the indoor environment comprises accessing the first timeseries of pathogen data comprising:

a first pathogen level of the first pathogen detected in a first pathogen sample, in the series of pathogen samples, collected from the indoor environment during a first sampling period within the first time period; and a second pathogen level of the first pathogen detected in a second pathogen sample, in the series of pathogen samples, collected from the indoor environment during a second sampling period, succeeding the first sampling period, within the first time period; and further comprising:

calculating a correlation between the first pathogen profile and the baseline pathogen profile; and predicting a third pathogen level of the first pathogen in a third pathogen sample collected during a third sampling period succeeding the second sampling period based on the first pathogen profile and the correlation.

17. The method of claim 16, further comprising, in response to the third pathogen level exceeding a threshold pathogen level defined for the first pathogen in the indoor environment:

generating a notification indicating prediction of the third
pathogen level of the first pathogen during the sampling
period; and transmitting the notification to a user associated with the
indoor environment.

18. The method of claim 12:

wherein accessing the baseline pathogen profile com-
prises accessing the baseline pathogen profile compris-
ing:
a first preceding pathogen profile of the first pathogen;
and
a second preceding pathogen profile of a second patho-
gen in the set of pathogens;
wherein characterizing the first difference between the
first pathogen profile and the baseline pathogen profile
comprises characterizing the first difference between
the first pathogen profile and the first preceding patho-
gen profile;
further comprising:
accessing a second timeseries of pathogen data for the
second pathogen and derived from the series of
pathogen samples;
characterizing a second pathogen profile, in the first set
of pathogen profiles, of the indoor environment
during the first time period based on the second
timeseries of pathogen data, the second pathogen
profile representative of changes in pathogen level of
the second pathogen in the indoor environment dur-
ing the first time period; and
characterizing a second difference between the second
pathogen profile and the second preceding pathogen
profile; and
wherein selecting the first mitigation action based on the
first difference comprises:
in response to the first difference exceeding the thresh-
old difference and the second difference falling
below the threshold difference, selecting the first
mitigation action;
in response to the second difference exceeding the
threshold difference and the first difference falling
below the threshold difference, selecting a second
mitigation action, in the set of mitigation actions,
configured to reduce pathogen levels of the second
pathogen; and

34 in response to the first difference exceeding the thresh-
old difference and in response to the second differ-
ence exceeding the threshold difference, selecting a
third mitigation action, in the set of mitigation
actions, configured to reduce pathogen levels of the
first pathogen and the second pathogen.

19. The method of claim 12:

further comprising accessing a first timeseries of envi-
ronmental data corresponding to a set of environmental
conditions in the indoor environment during the first
time period; and wherein accessing the baseline pathogen profile com-
prises:
accessing a pathogen model linking the set of environ-
mental conditions to detected pathogen levels of the
set of pathogens in the indoor environment; and
calculating the baseline pathogen profile based on the
first timeseries of environmental data and the patho-
gen model.

20. The method of claim 12, further comprising, in
response to transmitting the prompt to implement the first
mitigation action to the user:

accessing a second timeseries of pathogen data for the
first pathogen and derived from a second series of
pathogen samples collected from the indoor environ-
ment during a second time period succeeding the first
time period;

characterizing a second pathogen profile for the indoor
environment during the second time period based on
the second timeseries of pathogen data;

characterizing a reduction of the first pathogen in the
indoor environment based on a difference between the
second pathogen profile and the first pathogen profile;

in response to the reduction of the first pathogen exceed-
ing a threshold reduction, confirming efficacy of the
first mitigation action; and in response to the reduction falling below the threshold
reduction, selecting a second mitigation action in
replacement of the first mitigation action, configured to
mitigate pressures of the first pathogen in the indoor
environment.

* * * * *